(12) United States Patent
Rajadurai et al.

(10) Patent No.: US 10,499,245 B2
(45) Date of Patent: Dec. 3, 2019

(54) METHOD FOR PERFORMING MULTIPLE AUTHENTICATIONS WITHIN SERVICE REGISTRATION PROCEDURE

(71) Applicant: Samsung Electronics Co., Ltd., Suwon-si, Gyeonggi-do (KR)

(72) Inventors: Rajavelsamy Rajadurai, Bangalore (IN); Basavaraj Jayawant Pattan, Bangalore (IN); Suresh Chitturi, Bangalore (IN)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/565,801

(22) PCT Filed: Apr. 12, 2016

(86) PCT No.: PCT/KR2016/003860
§ 371 (c)(1),
(2) Date: Oct. 11, 2017

(87) PCT Pub. No.: WO2016/167553
PCT Pub. Date: Oct. 20, 2016

(65) Prior Publication Data
US 2018/0124604 A1  May 3, 2018

(30) Foreign Application Priority Data

Apr. 13, 2015 (IN) ............................ 1921/CHE/2015
Apr. 11, 2016 (IN) ............................ 1921/CHE/2015

(51) Int. Cl.
*H04W 12/06* (2009.01)
*H04W 4/10* (2009.01)
(Continued)

(52) U.S. Cl.
CPC ......... *H04W 12/06* (2013.01); *H04L 65/1016* (2013.01); *H04L 65/1073* (2013.01);
(Continued)

(58) Field of Classification Search
CPC ..... H04W 12/06; H04W 4/90; H04W 60/005; H04W 76/45; H04W 12/08; H04W 4/10;
(Continued)

(56) References Cited

U.S. PATENT DOCUMENTS 8,055,262 B1   11/2011   Vu et al.
9,730,092 B2    8/2017   Jung et al.
(Continued)

FOREIGN PATENT DOCUMENTS

WO   2015-050395 A1   4/2015

OTHER PUBLICATIONS

3GPP, TSG SA, Mission Critical Push to Talk (MCPTT) over LTE, Stage 1, (Release 13), 3GPP TS 22.179 V13.1.0, Mar. 21, 2015, (http://www.3gpp.org/DynaReport/22179.htm).
(Continued)

*Primary Examiner* — Christopher M Brandt
(74) *Attorney, Agent, or Firm* — Jefferson IP Law, LLP

(57) ABSTRACT

Embodiments herein provide a method for performing multiple authentications within a service registration procedure. The method includes sending, by a User Equipment (UE) a REGISTER request message to an IP Multimedia Subsystem (IMS) server. Further, the method includes receiving, an IMS authentication challenge from the IMS server, where the IMS authentication challenge includes an IMS authentication parameter and a MCPTT authentication challenge. Further, the method includes verifying, at the UE, the IMS authentication challenge. Further, the method includes generating, at the UE, a REGISTER response message. Further, the method includes sending, a REGISTER response mes-
(Continued)

sage to the IMS server, where the REGISTER response message includes an IMS authentication response to authenticate UE at the IMS server and a MCPTT authentication response to authenticate the UE at the MCPTT server.

12 Claims, 12 Drawing Sheets

(51) Int. Cl.
*H04L 29/06* (2006.01)
*H04W 4/90* (2018.01)
(52) U.S. Cl.
CPC ........... *H04L 65/4061* (2013.01); *H04W 4/10* (2013.01); *H04W 4/90* (2018.02)
(58) Field of Classification Search
CPC ............. H04L 65/1073; H04L 65/4061; H04L 65/1016; H04L 29/06
See application file for complete search history.

(56) References Cited

U.S. PATENT DOCUMENTS

2009/0247129 A1* 10/2009 Lee ...................... G06Q 20/02
455/411
2016/0344726 A1* 11/2016 Stojanovski .......... H04W 76/10
2017/0289776 A1* 10/2017 Kim ........................ H04W 4/08

OTHER PUBLICATIONS

3GPP, TSG SA, Study on Security Enhancements for Mission Critical Push to Talk (MCPTT) over LTE (Release 13), 3GPP TR 33.879 V0.1.0, Feb. 6, 2015, (http://www.3gpp.org/DynaReport/33879.htm).
Blackberry UK LTD.; Addition of Registration procedure for Solution 2-1; 3GPP TSG-SA WG6 Meeting #3; S6-150216; Feb. 25-27, 2015; Sophia Antipolis, FR.
3GPP; 3rd Generation Partnership Project; Technical Specification Group Services and System Aspects; Study on application architecture to support Mission Critical Push to Talk over LTE (MCPTT) services; (Release 13); 3GPP TR 23.779; V0.6.0; Mar. 2015; Valbonne, FR.
TD Tech et al.; Log on and authentication for MCPTT applications; 3GPP TSG-SA WG6 Meeting #3; S6-150204; Apr. 13-17, 2015; San Jose del Cabo, MX.
Rajavelsamy et al.; Efficient Registration Procedure for Multi-Domain Authentication for Mission Critical Communication Services; 2015 IEEE Conference on Standards for Communications and Networking (CSCN); 2015.

* cited by examiner

[Fig. 1a]
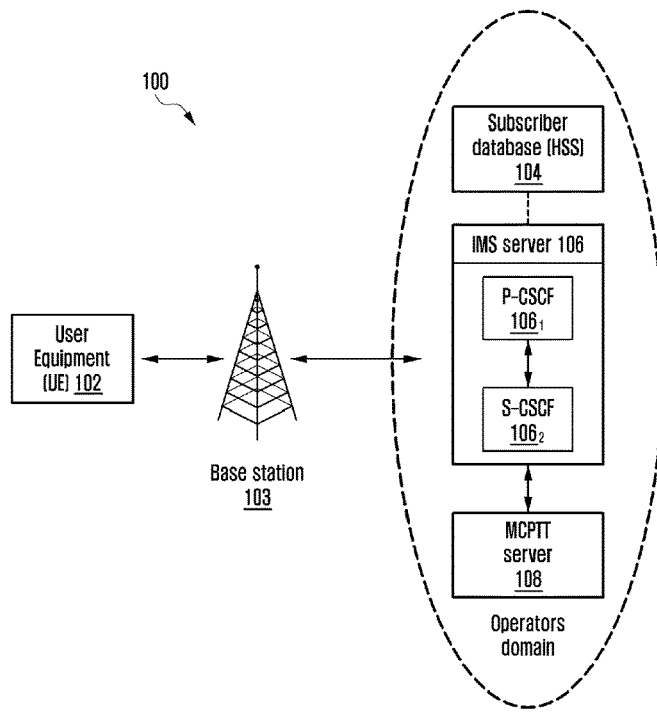
[Fig. 1b]
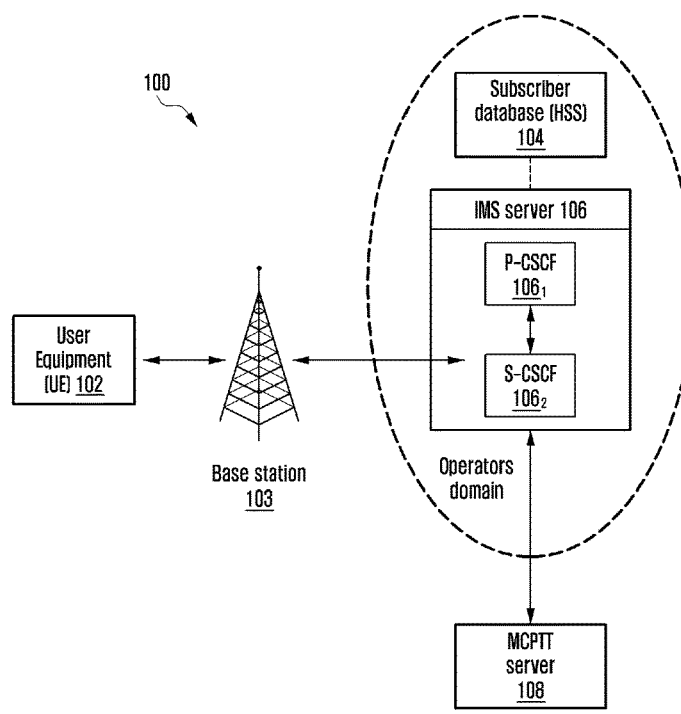

[Fig. 1c]
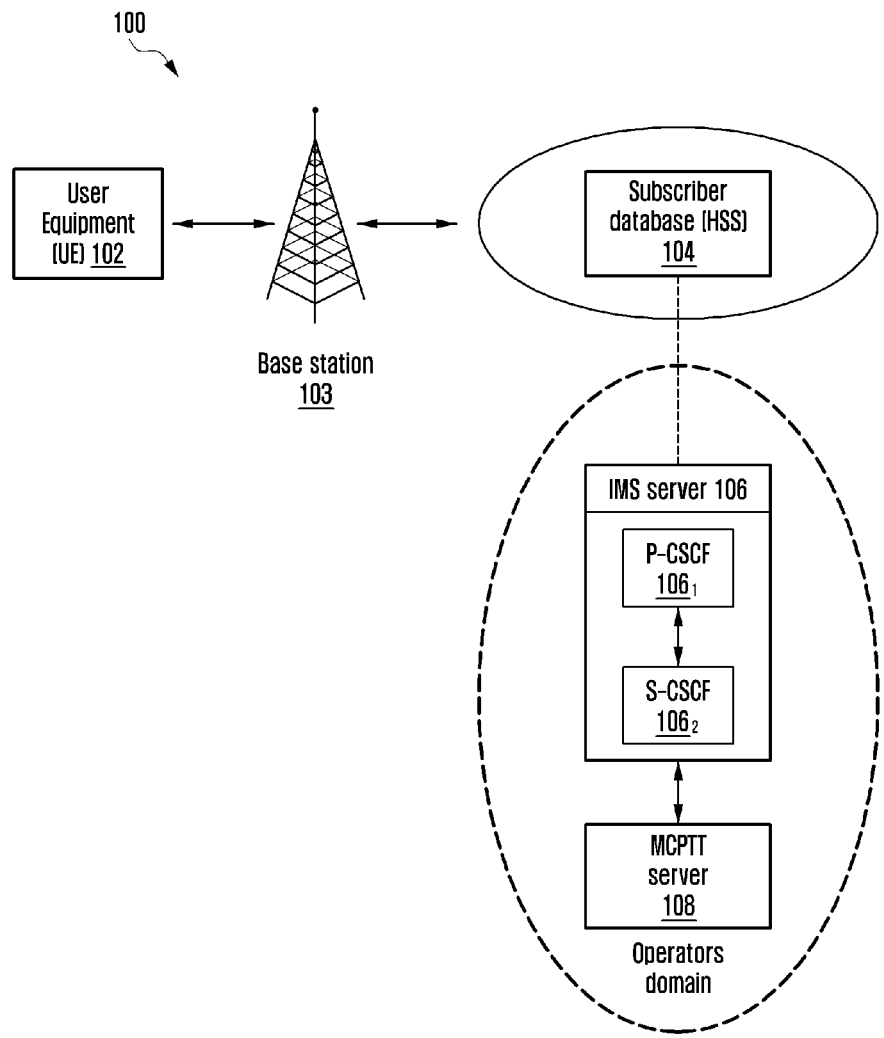

[Fig. 2]
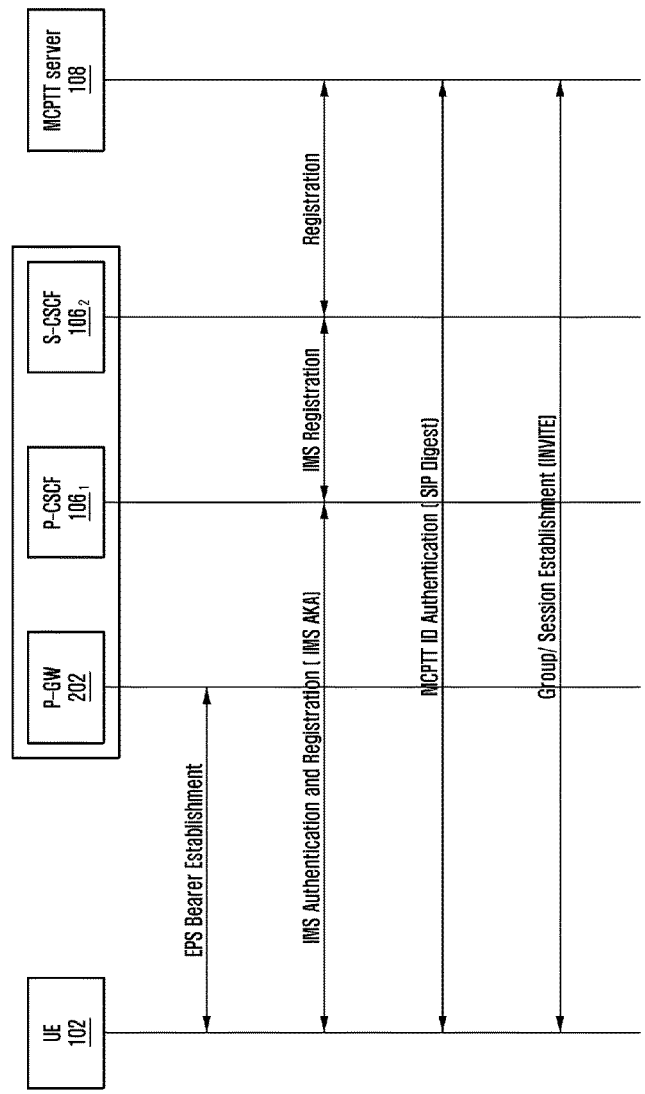
[Fig. 3a]
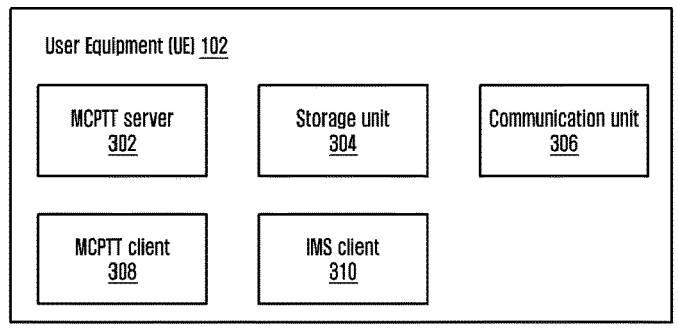

[Fig. 3b]
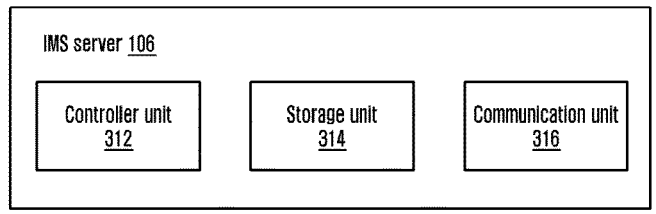
[Fig. 4]
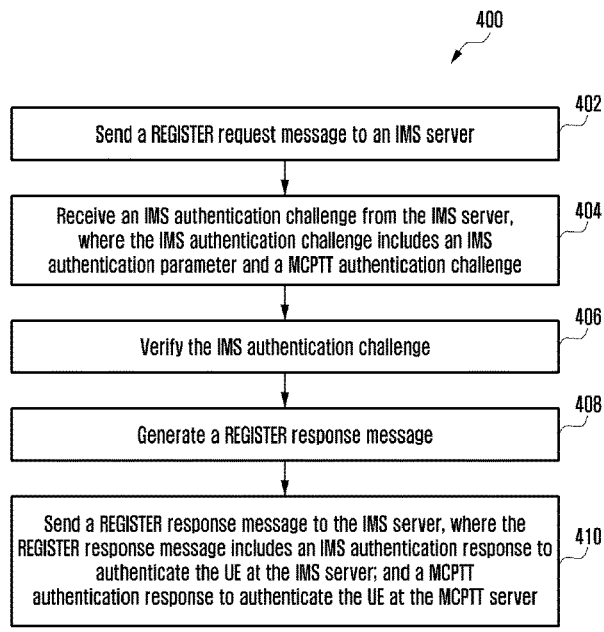
[Fig. 5]
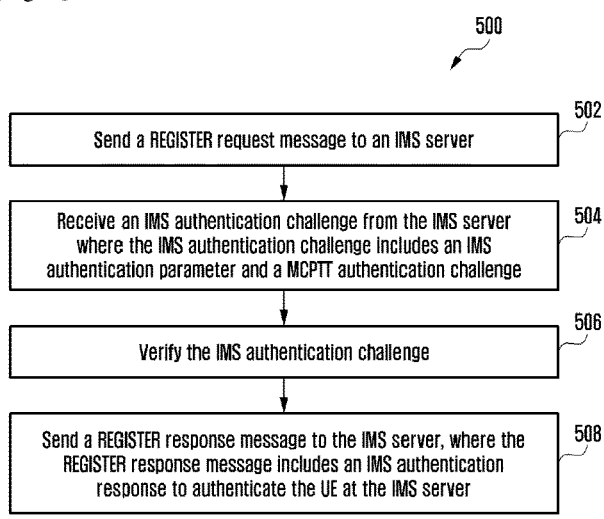

[Fig. 6]
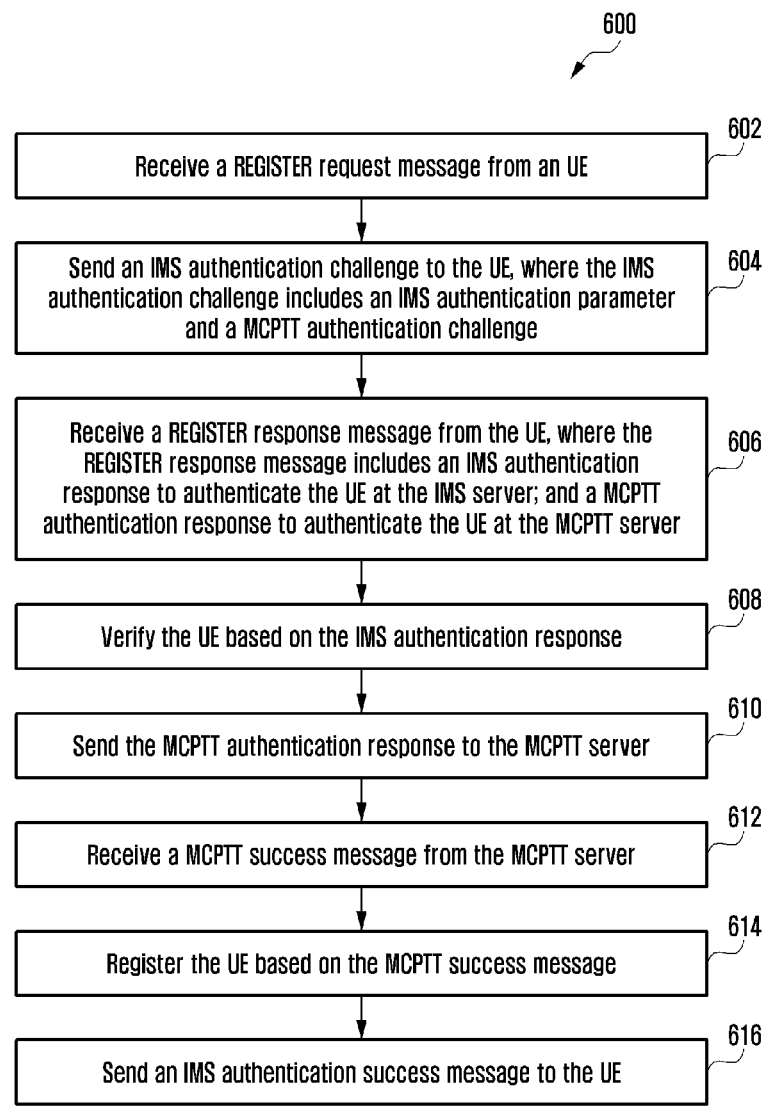

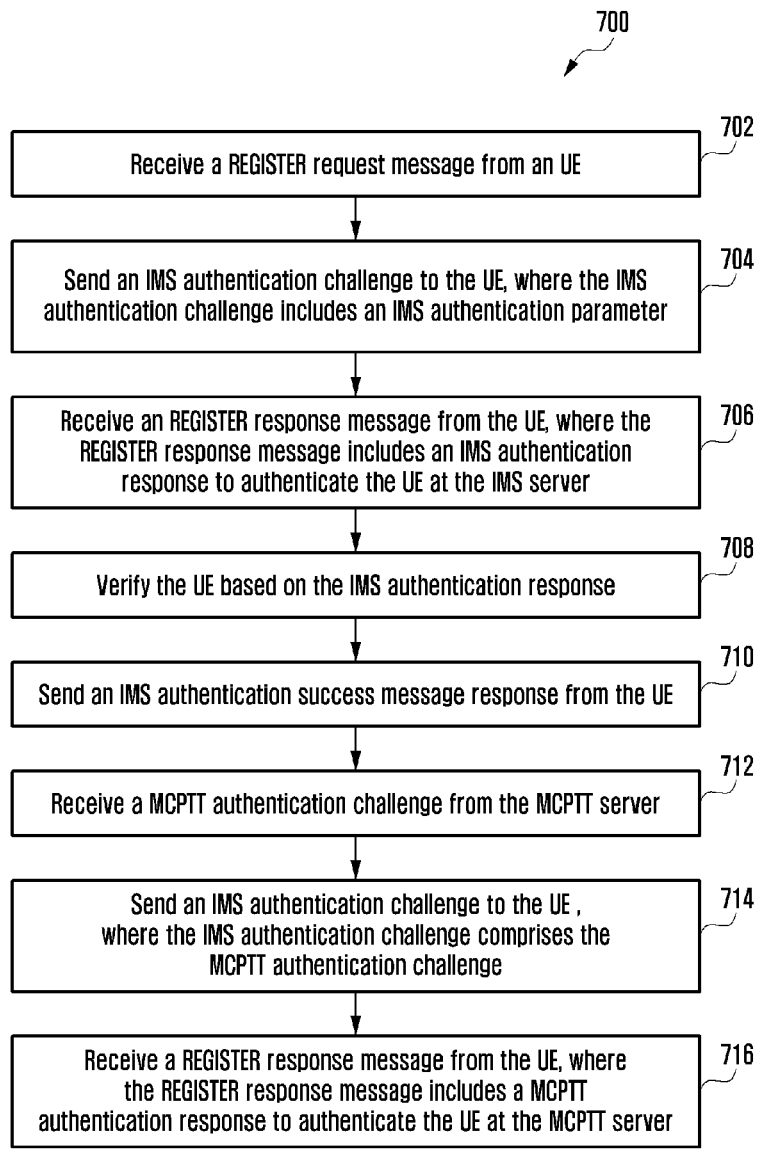

[Fig. 8]
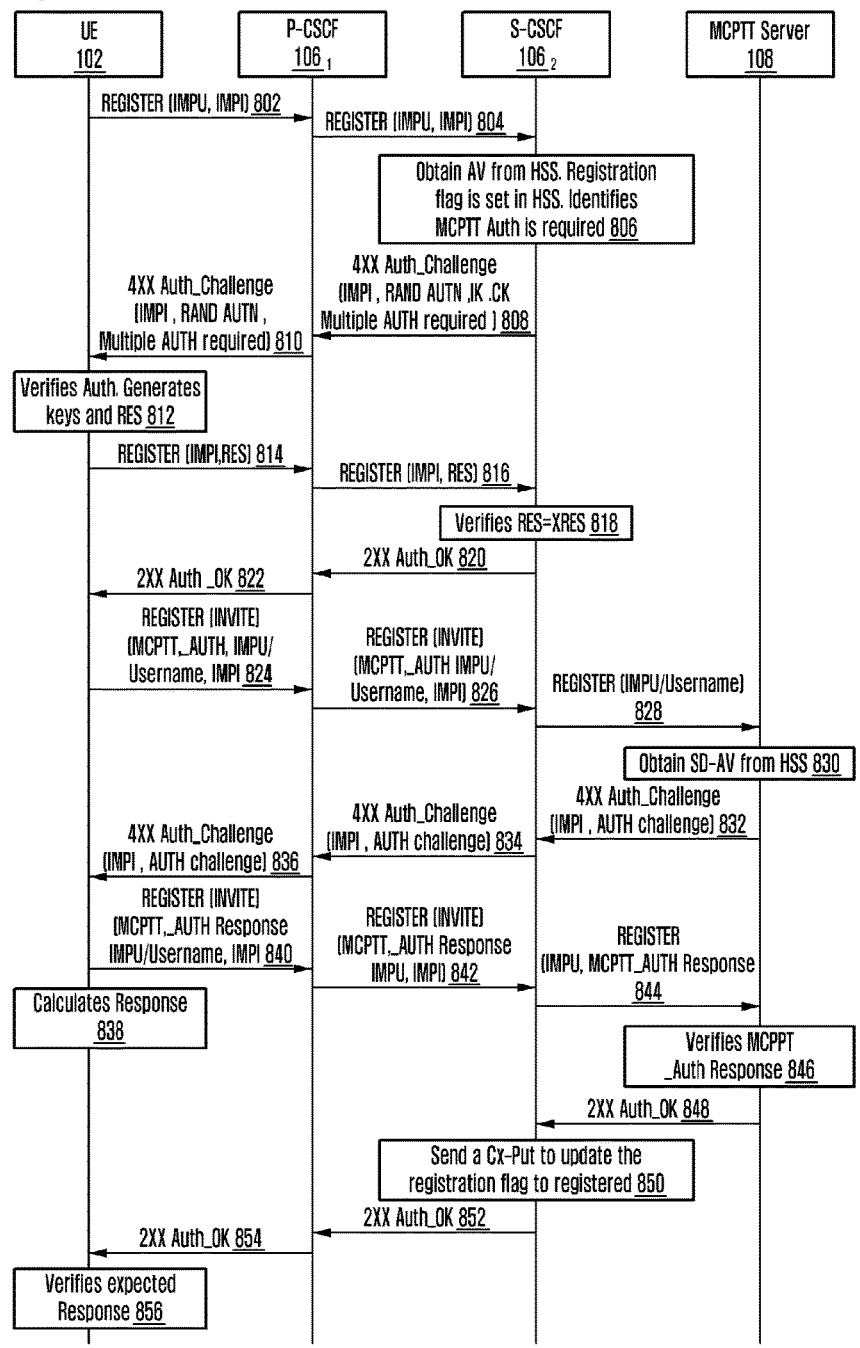

[Fig. 9]
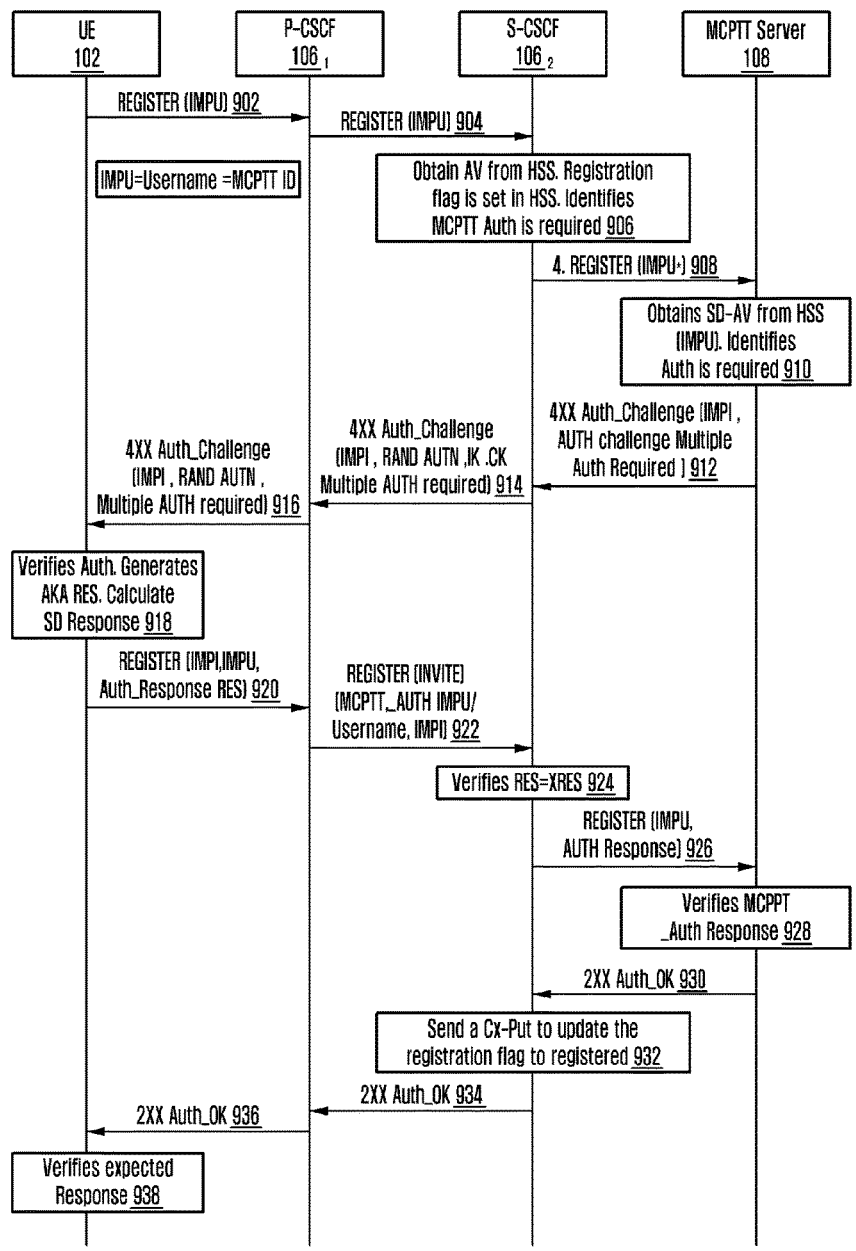

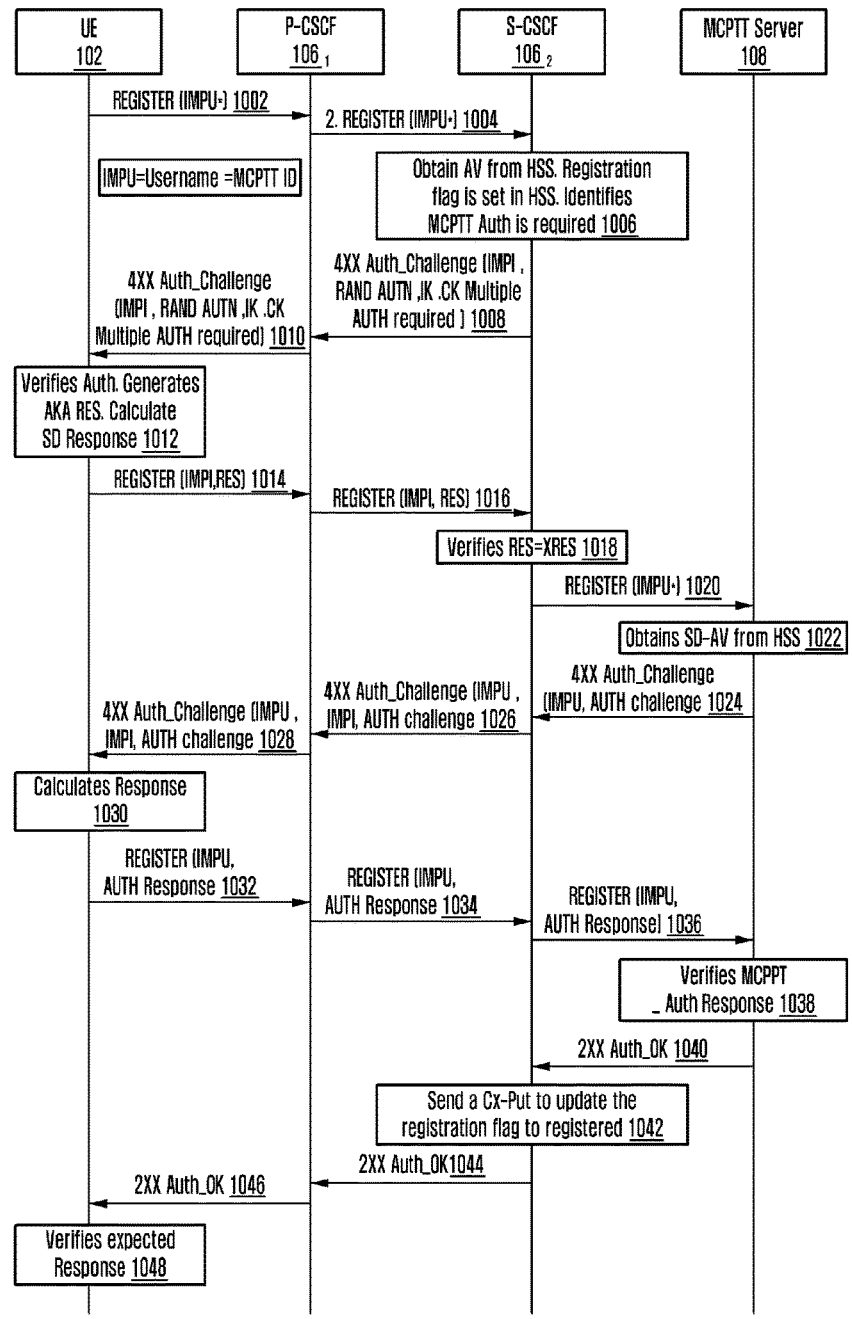
[Fig. 10]

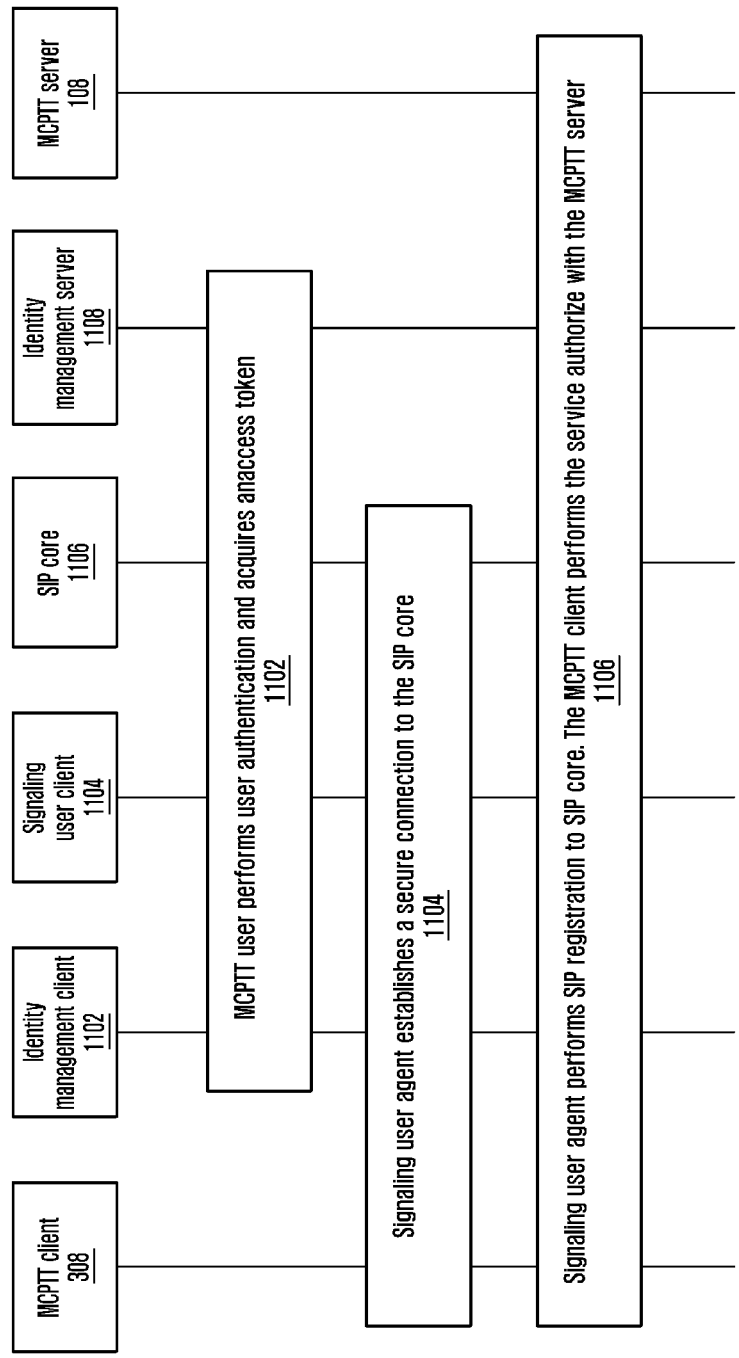
[Fig. 11]

[Fig. 12a]
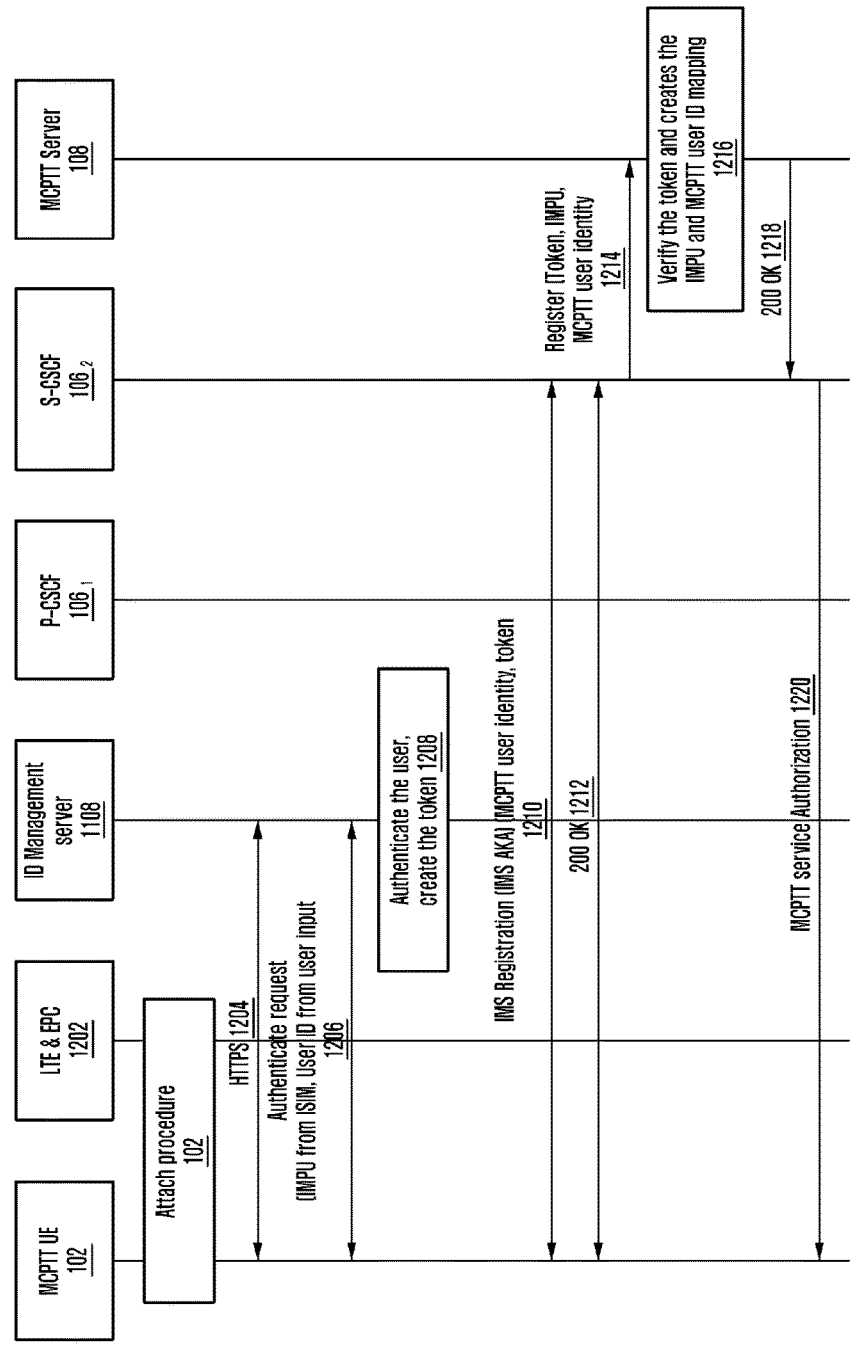

[Fig. 12b]
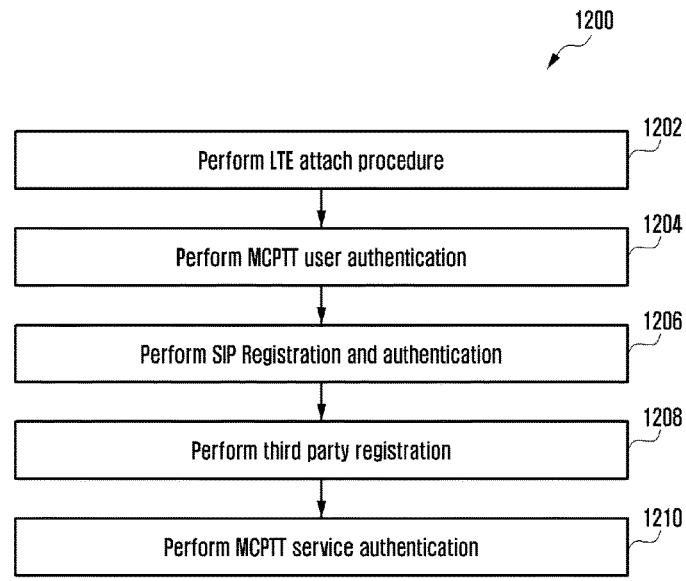
[Fig. 13]
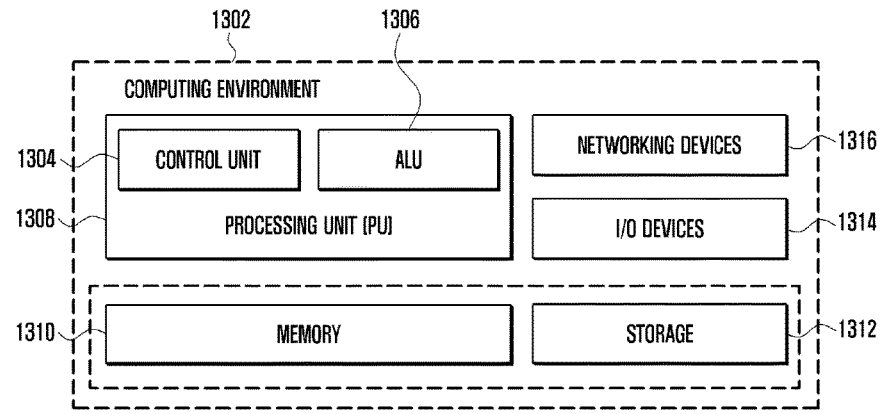

METHOD FOR PERFORMING MULTIPLE AUTHENTICATIONS WITHIN SERVICE REGISTRATION PROCEDURE

TECHNICAL FIELD

The embodiments herein relate generally to wireless communication systems. More particularly, related to a mechanism for performing multiple authentications within a service registration procedure. The present application is based on, and claims priority from an Indian Application Number 1921/CHE/2015 filed on 13 Apr., 2015, the disclosure of which is hereby incorporated by reference herein.

BACKGROUND ART

The 3rd Generation Partnership Project (3GPP) decided to establish a standard for Mission Critical Push-to-Talk (MCPTT) Communications over Long-Term Evolution (LTE) (for Release 13). MCPTT systems utilized by public safety (PS) agencies enable their personnel to selectively and sequentially transmit messages to one another, either on a one-to-one or one-to-many basis over LTE. MCPTT service domain is usually operated by an entity (PS agency) different from the entity operating LTE and IP Multimedia Subsystem (IMS) domain. In such cases, each domain may have to provide their own identity and execute their own security mechanisms to ensure authenticity and privacy of the PS users, while adhering to stringent call setup time requirements.

There are significant efforts in considering a Session Initiation Protocol (SIP) Core based Architecture for the MCPTT Applications. In the IMS, authentication of the subscriber is performed during the registration procedures. Currently defined IMS/SIP registration procedures includes single authentication to complete the IP-based service registration procedure. The application level registration is performed using third party registration, and after IP connectivity for the signaling has been gained from the access network. In case if a separate application level authentication is needed, then currently there is no solution available in the IMS specifications.

For MCPTT service, it is required to perform separate authentication in addition to the IMS authentication. This is due to isolation of MCPTT credentials from the SIP core credentials and due to different service providers.

Further, in some scenarios it is required to have multiple authentications to register for the IP-based service. Especially, when the IMS is owned by the mobile operator and MCPTT service is owned by public safety agency. Considering the following illustrative scenarios, where the PS agency or the Mobile network Operator (LTE) Administrates MCPTT System and/or SIP core:

In some cases, if the MCPTT capable UE is shared (sharable UE). The sharable MCPTT UE is a pool of UE's wherein each UE being interchangeable with any other, and users randomly choosing one or more UE's from the pool of UE's, each user for temporary exclusive use. The shareable MCPTT UE can be used by the user who can gain access to the MCPTT client application stored therein and can become an authenticated MCPTT user.

Based on the MCPTT security requirements and scenarios, multiple authentications (IP-based service access level and also application level (MCPTT) within the registration process needs to be performed.

Thus, there is a need of a simple and robust mechanism for performing multiple (IMS and MCPTT) authentications within the single SIP registration process. Especially for the scenarios, where application layer signaling network for session initiation/control/management and the application server are administrated by different providers/operators.

The above information is presented as background information only to help the reader to understand the present invention. Applicants have made no determination and make no assertion as to whether any of the above might be applicable as Prior Art with regard to the present application.

DISCLOSURE OF INVENTION

Technical Problem

The principal object of the embodiments herein is to provide a mechanism for performing multiple (IMS and MCPTT) authentications within a service registration procedure.

Another object of the embodiments herein is to provide a mechanism for sending, by a User Equipment (UE), a REGISTER request message to an IMS server.

Another object of the embodiments herein is to provide a mechanism for receiving, at the UE, authentication challenge from the IMS server, where the authentication challenge includes an IMS authentication parameter and a MCPTT authentication challenge.

Another object of the embodiments herein is to provide a mechanism for verifying, at the UE, the IMS authentication challenge.

Another object of the embodiments herein is to provide a mechanism for generating, at the UE, a REGISTER response message.

Another object of the embodiments herein is to provide a mechanism for sending, by the UE, the REGISTER response message to the IMS server, where the REGISTER response message includes an IMS authentication response to authenticate the UE at the IMS server and a MCPTT authentication response to authenticate the UE at the MCPTT server.

Another object of the embodiments herein is to provide a mechanism for sending, by a User Equipment (UE), a REGISTER request message to an IMS server.

Another object of the embodiments herein is to provide a mechanism for receiving, at the UE, an IMS authentication challenge from the IMS server, where the IMS authentication challenge includes an IMS authentication parameter and a MCPTT authentication indication.

Another object of the embodiments herein is to provide a mechanism for verifying, at the UE, the IMS authentication challenge.

Another object of the embodiments herein is to provide a mechanism for sending, by the UE, a REGISTER response message to the IMS server, where the REGISTER response message includes an IMS authentication response to authenticate the UE at the IMS server.

Another object of the embodiments herein is to provide a mechanism for receiving, at an IMS server, a REGISTER request message from an UE Another object of the embodiments herein is to provide a mechanism for sending, by the IMS server, an IMS authentication challenge to the UE, where the IMS authentication challenge includes an IMS authentication parameter and a MCPTT authentication challenge.

Another object of the embodiments herein is to provide a mechanism for receiving, at the IMS server, a REGISTER response message from the UE, where the REGISTER response message includes an IMS authentication response to authenticate the UE at the IMS server and a MCPTT authentication response to authenticate the UE at the MCPTT server.

Another object of the embodiments herein is to provide a mechanism for receiving, at an IMS server, a REGISTER request message from an UE.

Another object of the embodiments herein is to provide a mechanism for sending, by the IMS server, an IMS authentication challenge to the UE, where the IMS authentication challenge includes an IMS authentication parameter.

Another object of the embodiments herein is to provide a mechanism for receiving, at the IMS server, a REGISTER response message from the UE, where the REGISTER response message includes an IMS authentication response to authenticate the UE at the IMS server.

Solution to Problem

Accordingly the embodiments herein provide a method for performing multiple authentications within a service registration procedure. The method includes sending, by a User Equipment (UE), a REGISTER request message to an IMS server. Further, the method includes receiving, at the UE, an IMS authentication challenge from the IMS server, where the IMS authentication challenge includes an IMS authentication parameter and a MCPTT authentication challenge. Further, the method includes verifying, at the UE, the IMS authentication challenge. Further, the method includes generating, at the UE, a REGISTER response message. Furthermore, the method includes sending, by the UE, the REGISTER response message to the IMS server, where the REGISTER response message includes an IMS authentication response to authenticate the UE at the IMS server and a MCPTT authentication response to authenticate the UE at the MCPTT server.

Accordingly the embodiments herein provide a method performing multiple authentications within a service registration procedure. The method includes sending, by an UE, a REGISTER request message to an IMS server. Further, the method includes receiving, at the UE, an IMS authentication challenge from the IMS server, where the IMS authentication challenge includes an IMS authentication parameter and a MCPTT authentication indication. Further, the method includes verifying, at the UE, the IMS authentication challenge. Further, the method includes sending, by the UE, a REGISTER response message to the IMS server, where the REGISTER response message includes an IMS authentication response to authenticate the UE at the IMS server.

Accordingly the embodiments herein provide a method performing multiple authentications within a service registration procedure. The method includes receiving, at an IMS server, a REGISTER request message from an UE. Further, the method includes sending, by the IMS server, an IMS authentication challenge to the UE, where the IMS authentication challenge includes an IMS authentication parameter and a MCPTT authentication challenge. Further, the method includes receiving, at the IMS server, a REGISTER response message from the UE, where the REGISTER response message includes an IMS authentication response to authenticate the UE at the IMS server and a MCPTT authentication response to authenticate the UE at the MCPTT server. Furthermore, the method includes receiving, at an IMS server, a REGISTER request message from an UE.

Accordingly the embodiments herein provide a method performing multiple authentications within a service registration procedure. The method includes receiving, at an IMS server, a REGISTER request message from an UE. Further, the method includes sending, by the IMS server, an IMS authentication challenge to the UE, where the IMS authentication challenge includes an IMS authentication parameter. Further, the method includes receiving, at the IMS server, a REGISTER response message from the UE, where the REGISTER response message includes an IMS authentication response to authenticate the UE at the IMS server.

Accordingly the embodiments herein provide a User Equipment (UE) for performing multiple authentications within a service registration procedure. The UE includes a storage unit and a controller unit, coupled to the storage unit, configured to send a REGISTER request message to an IP Multimedia Subsystem (IMS) server. Further, the controller can be configured to receive an IMS authentication challenge from the IMS server, wherein the IMS authentication challenge comprises an IMS authentication parameter and a Mission Critical Push to Talk (MCPTT) authentication challenge. Further, the controller unit can be configured to verify the IMS authentication challenge and MCPTT authentication challenge. Further, the controller unit can be configured to generate a REGISTER response message. Further, the controller unit can be configured to send the REGISTER response message to the IMS server, wherein the REGISTER response message comprises an IMS authentication response to authenticate the UE at the IMS server, and a MCPTT authentication response to authenticate the UE at the MCPTT server.

Accordingly the embodiments herein provide a User Equipment (UE) for performing multiple authentications within a service registration procedure. The UE includes a storage unit and a controller unit, coupled to the storage unit, configured to send a REGISTER request message to an IP Multimedia Subsystem (IMS) server. Further, the controller can be configured to receive an IMS authentication challenge from the IMS server, wherein the IMS authentication challenge comprises an IMS authentication parameter and a Mission Critical Push to Talk (MCPTT) authentication indication. Further, the controller unit can be configured to verify the IMS authentication challenge. Further, the controller unit can be configured to send a REGISTER response message to said IMS server, wherein said REGISTER response message comprises an IMS authentication response to authenticate the UE at the IMS server.

Accordingly the embodiments herein provide an IP Multimedia Subsystem (IMS) server for performing multiple authentications within a service registration procedure. The IP Multimedia Subsystem (IMS) server includes a storage unit and a controller unit, coupled to the storage unit, configured to receive a REGISTER request message from an UE. Further, the controller unit can be configured to send an IMS authentication challenge to the UE, wherein the IMS authentication challenge comprises an IMS authentication parameter and a MCPTT authentication challenge. Further, the controller unit can be configured to receive a REGISTER response message from the UE, wherein the REGISTER response message comprises an IMS authentication response to authenticate the UE at the IMS server; and a MCPTT authentication response to authenticate the UE at the MCPTT server.

Accordingly the embodiments herein provide an IP Multimedia Subsystem (IMS) server for performing multiple authentications within a service registration procedure. The IP Multimedia Subsystem (IMS) server includes a storage unit and a controller unit, coupled to the storage unit, configured to receive a REGISTER request message from an UE. Further, the controller unit can be configured to send an IMS authentication challenge to the UE, where the IMS authentication challenge comprises an IMS authentication parameter. Further, the controller unit can be configured to receive a REGISTER response message from the UE, wherein the REGISTER response message comprises an IMS authentication response to authenticate the UE at the IMS server.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

Advantageous Effects of Invention

The principal effect of the embodiments herein is to provide a mechanism for performing multiple (IMS and MCPTT) authentications within a service registration procedure.

Another effect of the embodiments herein is to provide a mechanism for sending, by a User Equipment (UE), a REGISTER request message to an IMS server.

BRIEF DESCRIPTION OF DRAWINGS

This invention is illustrated in the accompanying drawings, throughout which like reference letters indicate corresponding parts in the various figures. The embodiments herein will be better understood from the following description with reference to the drawings, in which:

FIGS. 1a-1b illustrates a Public Safety Administration of a MCPTT System.

FIG. 1c illustrates a Public Safety Administration of a MCPTT Application and SIP Core.

FIG. 2 illustrates a sequence diagram performing SIP digest based authentication for both IMS and MCPTT authentication.

FIG. 3a shows various units of a User Equipment (UE) for performing multiple authentications within a service registration procedure, according to an embodiment as disclosed herein;

FIG. 3b shows various units of an IMS server for performing multiple authentications within a service registration procedure, according to an embodiment as disclosed herein FIG. 4 is a flow diagram illustrating a method for performing an IMS Authentication (Auth) and a MCPTT Authentication (Auth) by a UE, according to an embodiment as disclosed herein;

FIG. 5 is a flow diagram illustrating a method for performing an IMS Auth and MCPTT Auth sequentially by a UE, according to an embodiment as disclosed herein;

FIG. 6 is a flow diagram illustrating a method for performing an IMS Authentication (Auth) and a MCPTT Authentication (Auth) by an IMS server, according to an embodiment as disclosed herein;

FIG. 7 is a flow diagram illustrating a method for performing an IMS Auth and MCPTT Auth sequentially by an IMS server, according to an embodiment as disclosed herein;

FIG. 8 illustrates a sequence diagram performing IMS Authentication and MCPTT Authentication sequentially, according to an embodiment as disclosed herein;

FIG. 9 illustrates a sequence diagram performing (i.e, simultaneously) IMS Authentication and MCPTT Authentication, according to an embodiment as disclosed herein;

FIG. 10 illustrates a sequence diagram performing MCPTT Authentication after successful IMS Authentication, according to an embodiment as disclosed herein;

FIG. 11 illustrates a sequence diagram describing an example of call flow for MCPTT service authentication, according to an embodiment as disclosed herein;

FIG. 12a illustrates a sequence diagram describing an example for performing MCPTT user authentication and registration, according to an embodiment as disclosed herein;

FIG. 12b is a flow diagram illustrating a method for MCPTT service registration, according to an embodiment as disclosed herein; and FIG. 13 illustrates a computing environment implementing the method for performing multiple authentications within a service registration procedure, according to embodiments as disclosed herein.

MODE FOR THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The embodiments disclose a method for performing multiple authentications within a service registration procedure. The method includes sending, by a User Equipment (UE), a REGISTER request message to an IMS server. Further, the method includes receiving, at the UE, an IMS authentication challenge from the IMS server, where the IMS authentication challenge includes an IMS authentication parameter and a MCPTT authentication challenge. Further, the method includes verifying, at the UE, the IMS authentication challenge. Further, the method includes generating, at the UE, a REGISTER response message. Furthermore, the method includes sending, by the UE, the REGISTER response message to the IMS server, where the REGISTER response message includes an IMS authentication response to authenticate the UE at the IMS server and a MCPTT authentication response to authenticate the UE at the MCPTT server.

In an embodiment, the IMS authentication parameter includes at least one of RAND, AUTN, and MCPTT authentication indication.

The embodiments herein disclose a method for performing multiple authentications within a service registration procedure. The method includes sending, by the UE, a REGISTER request message to an IMS server. The method includes receiving, at the UE, the IMS authentication challenge from the IMS server, where the IMS authentication challenge includes an IMS authentication parameter and a MCPTT authentication indication. Further, the method includes verifying, at the UE, the IMS authentication challenge and sending, by the UE, the REGISTER response message to the IMS server, where the REGISTER response message includes the IMS authentication response to authenticate the UE at the IMS server.

In an embodiment, the method further includes receiving, at the UE, the IMS authentication success message. Further, the method includes sending, by the UE, the REGISTER request message to the IMS server. Further, the method includes receiving, at the UE, the IMS authentication challenge from the IMS server, wherein the IMS authentication challenge includes an authentication parameter associated with the IMS server and the MCPTT authentication challenge. Further, the method includes verifying, at the UE, the IMS authentication challenge. Further, the method includes sending, by the UE, a REGISTER response message to the IMS server, wherein the REGISTER response message comprises a MCPTT authentication response to authenticate the UE at the MCPTT server.

Accordingly the embodiments herein provide a method performing multiple authentications within a service registration procedure. The method includes receiving, at an IMS server, a REGISTER request message from an UE. Further, the method includes sending, by the IMS server, an IMS authentication challenge to the UE, where the IMS authentication challenge includes an IMS authentication parameter and a MCPTT authentication challenge. Further, the method includes receiving, at the IMS server, a REGISTER response message from the UE, where the REGISTER response message includes an IMS authentication response to authenticate the UE at the IMS server and a MCPTT authentication response to authenticate the UE at the MCPTT server. Furthermore, the method includes receiving, at an IMS server, a REGISTER request message from an UE. Further, the method includes sending, by the IMS server, an IMS authentication challenge to the UE, wherein the IMS authentication challenge comprises an IMS authentication parameter and a MCPTT authentication challenge. Further, the method includes receiving, at the IMS server, a REGISTER response message from the UE, wherein the REGISTER response message includes an IMS authentication response to authenticate the UE at the IMS server and a MCPTT authentication response to authenticate the UE at the MCPTT server.

Accordingly the embodiments herein provide a method performing multiple authentications within a service registration procedure. The method includes receiving, at an IMS server, a REGISTER request message from an UE. Further, the method includes sending, by the IMS server, an IMS authentication challenge to the UE, where the IMS authentication challenge includes an IMS authentication parameter. Further, the method includes receiving, at the IMS server, a REGISTER response message from the UE, where the REGISTER response message includes an IMS authentication response to authenticate the UE at the IMS server.

Referring now to the drawings, and more particularly to FIG. 1a through 13, where similar reference characters denote corresponding features consistently throughout the figures, there are shown preferred embodiments.

A Mission Critical Communications for Public Safety (PS) is of significant interest and high priority in the telecom industry (wireless communication systems), from various corridors such as national regulatory agencies, telecom service providers, network vendors and device manufacturers. With the growing interest within the public safety and critical communications community of securing LTE as the next-generation platform for public safety communications, over traditional narrowband technologies such as Project 25 (P25) and Terrestrial Trunked Radio (TETRA) systems, 3GPP has established a new working group (SA6) and a corresponding work-item (Mission Critical Push To Talk? MCPTT) for Release 13. Further, While PS-Long Time Evolution (LTE) (Public Safety over LTE) standards are already in development within 3GPP with initiatives such as ProSe (Proximity Services) and GCSE (Group Communication Services Enabler) since 3GPP Release 12, MCPTT is responsible for developing the overall application and service layer aspects of mission critical applications. It is however, expected that MCPTT will utilize the underlying technologies such as IMS, LTE Device to Device Proximity Services (ProSe) and Group Communication System Enablers for LTE (GCSE_LTE) as necessary in order to realize the MCPTT requirements.

However, the existing SIP registration procedure which is considered as the signaling protocol for the MCPTT is suitable only in scenarios where the IMS and the Application Service domains belong to the same operator or at least a mutual trust is established between the operators of two domains. Hence for MCPTT service operated within multiple domains (signaling plane and application plane are operated by different operators as described in FIGS. 1a-1c.

The FIGS. 1a-1c illustrates a system 100 of a Public Safety Administration of the MCPTT System. The system 100 includes a User Equipment (UE) 102, a subscriber database (HSS) 104, IMS server 106 and a MCPTT server 108. In an embodiment, the IMS server can be SIP registrars. In an another embodiment, the IMS server 106 includes a Proxy? call session control function (P-CSCF) 1061 and a secondary? call session control function (S-CSCF) 1062 as defined by the 3GPP technical specifications. In an embodiment, the system 100 can include at least one of a Mobility Management Entity (MME), a SGW/PGW. In an embodiment, the UE 102 can be a laptop, a desktop computer, a mobile phone, a mobile station, a mobile terminal, a smart phone, Personal Digital Assistants (PDAs), a tablet, a phablet, or any other electronic device. The UE 102 includes the applications (i.e., SIM, USIM, and ISIM).

The PS administration of the MCPTT System where the PS agency administers the MCPTT application represented by "MCPTT Domain". The LTE and the IMS Core Network (SIP Core) components are administered by the Mobile Network Operator (MNO) represented by the "Operator's Domain". The User Equipment (UE) shown can either be an open market device or a MNO customized device, equipped with an IP Multimedia Services Identity Module (ISIM) for IMS access and a Universal Subscriber Identity Module (USIM) for the LTE access within a single Universal Integrated Circuit Card (UICC). The UE is installed with the MCPTT client for MCPTT service access. This is a typical scenario that allows for the Public Safety Agencies with minimal or no resources to build out and operate their own network(s), are still able to provide MCPTT service with the help of existing commercial LTE networks.

The MCPTT service domain is usually operated by an entity (PS agency) different from the entity operating LTE (and IMS) domain. In such cases, each domain may have to provide identity to their users and execute their own security mechanisms to ensure authenticity and privacy of the PS users with stringent requirements on initial call setup time. Hence each domain needs to perform authentication for their respective domains. To establish the connection between an MCPTT UE and the MCPTT Application Service, authentication of the MCPTT user will be required, in addition to the IMS and the LTE authentication of the UE, i.e., to carry out two different operator domain authentications during SIP registration procedure, as shown in FIG. 2.

Unlike the conventional systems and methods described in the FIGS. 1a-1c and in the FIG. 2 the proposed method provides a mechanism for performing multiple authentications within a service registration procedure. Further, the proposed mechanism provides identity management and authentication across multiple domains, which is central to MCPTT architecture reducing the authentication delay that is essential to the increase the overall performance of the MCPTT service.

FIG. 3 shows various units of the UE 102 for performing multiple authentications within a service registration procedure, according to an embodiment as disclosed herein. In an embodiment, the UE 102 includes a controller unit 302, a storage unit 304, a communication unit 306, a MCPTT client unit 308 and an IMS client unit 310.

The controller unit 302 can be configured to send a REGISTER request message to an IMS server 106. In an embodiment, the REGISTER request message can include the Access Class, an International Mobile Subscriber Identity (IMSI), capability of the UE 102, an International Mobile Station Equipment Identity (IMEI), a Closed Subscriber Group (CSG) cell ID, or combination of same.

Further, the controller unit 302 can be configured to receive the IMS authentication challenge from the IMS server 106, where the IMS authentication challenge can include the IMS authentication parameter and the MCPTT authentication challenge.

Further, the controller unit 302 can be configured to verify the IMS authentication challenge. Further, the controller unit 302 can be configured to generate the REGISTER response message. Further, the controller unit can be configured 302 to send a REGISTER response message to the IMS server 106, where the REGISTER response message includes the IMS authentication response to authenticate the UE 102 at the IMS server 106 and a MCPTT authentication response to authenticate the UE 102 at the MCPTT server 108.

In an embodiment, the IMS authentication parameter includes at least one of RAND, AUTN, and MCPTT authentication indication.

Further, the controller unit 302 can be configured to receive the IMS authentication challenge from the IMS server 106, wherein the IMS authentication challenge can include the IMS authentication parameter and the MCPTT authentication indication.

Further, the controller unit 302 can be configured to receive the IMS authentication success message. Further, the controller unit 302 can be configured to send the REGISTER request message to the IMS server 106. Further, the controller unit 302 can be configured to receive the IMS authentication challenge from the IMS server 106, where the IMS authentication challenge can include the authentication parameter associated with the IMS server 106 and a MCPTT authentication challenge.

Further, the controller unit 302 can be configured to verify the IMS authentication challenge. Further, the controller unit 302 can be configured to send the REGISTER response message to the IMS server 106, where the REGISTER response message can include a MCPTT authentication response to authenticate the UE 102 at the MCPTT server 108.

Further, the controller unit 302 can be configured to verify the IMS authentication challenge. Further, the controller unit 302 can be configured to send a REGISTER response message to the IMS server, wherein the REGISTER response message comprises an IMS authentication response to authenticate the UE at the IMS server.

Further, the storage unit 304 may include one or more computer-readable storage media. The storage unit 304 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the storage unit 304 may, in some examples, be considered a non-transitory storage medium. The term "non-transitory" may indicate that the storage medium is not embodied in a carrier wave or a propagated signal. However, the term "non-transitory" should not be interpreted that the storage unit 304 is non-movable. In some examples, the storage unit 304 can be configured to store larger amounts of information than the memory. In certain examples, a non-transitory storage medium may store data that can, over time, change (e.g., in Random Access Memory (RAM) or cache). The communication unit 306 can be configured for communicating internally between the units and externally with the networks.

The communication unit 306 associated with the UE 102 provides the communication interface between the MCPTT client 308, the IMS client 310, the HSS 104, the IMS server 106 and the MCPTT server 108.

The MCPTT client 308 associated with the UE 102 controls the one or more actions associated with the MCPPT (MCPTT service). The one or more actions include for example, receiving request from other MCPTT clients, controlling the parameters associated with the MCPTT authentication in conjunction with the MCPTT sever 108, or the like.

The IMS client 310 associated with the UE 102 controls the one or more actions associated with the IMS (IMS service). The one or more actions includes for example, controlling the parameters associated with the IMS authentication in conjunction with the MCPTT sever 108, or the like.

The FIG. 3a shows example units of the UE 102 but it is to be understood that other embodiments are not limited thereon. In other embodiments, the UE 102 may include less or more number of units. Further, the labels or names of the units are used only for illustrative purpose and does not limit the scope of the invention. One or more units can be combined together to perform same or substantially similar function in the UE 102.

FIG. 3b shows various units of the IMS server 106 performing multiple authentications within the service registration procedure, according to an embodiment as disclosed herein. In an embodiment, the IMS server 106 can include a controller unit 312, a storage unit 314 coupled to the controller unit 312 and a communication unit 316 thereof.

The controller unit 312 can be configured to receive the REGISTER request message from the UE 102. Further, the controller unit 312 can be configured to send the IMS authentication challenge to the UE 102, wherein the IMS authentication challenge comprises the IMS authentication parameter and the MCPTT authentication challenge.

Further, the controller unit 312 can be configured to verify the IMS authentication challenge and send the REGISTER response message to the IMS server 106, wherein the REGISTER response message comprises the IMS authentication response to authenticate the UE 102 at the IMS server 106.

In another embodiment, the controller unit 312 can be configured to receive the REGISTER request message from the UE 102. Further, the controller unit 312 can be configured to send the IMS authentication challenge to the UE 102, wherein the IMS authentication challenge comprises the IMS authentication parameter and the MCPTT authentication challenge. Furthermore, the controller unit 312 can be configured to receive the REGISTER response message from the UE 102, wherein the REGISTER response message comprises the IMS authentication response to authenticate the UE 102 at the IMS server 106 and a MCPTT authentication response to authenticate the UE 102 at the MCPTT server 108.

In yet another embodiment, the controller unit 312 can be configured to receive the REGISTER request message from the UE 102. Further, the controller unit 312 can be configured to send the IMS authentication challenge to the UE 102, wherein the IMS authentication challenge comprises the IMS authentication parameter and receive the REGISTER response message from the UE 102, wherein the REGISTER response message comprises the IMS authentication response to authenticate the UE 102 at the IMS server 106.

Further, the storage unit 314 may include one or more computer-readable storage media. The storage unit 314 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the storage unit 314 may, in some examples, be considered a non-transitory storage medium. The term "non-transitory" may indicate that the storage medium is not embodied in a carrier wave or a propagated signal. However, the term "non-transitory" should not be interpreted that the storage unit 304 is non-movable. In some examples, the storage unit 314 can be configured to store larger amounts of information than the memory. In certain examples, a non-transitory storage medium may store data that can, over time, change (e.g., in Random Access Memory (RAM) or cache). The communication unit 316 can be configured for communicating internally between the units and externally with the networks.

Further, the communication unit 316 can be configured for communicating internally between the units and externally with the networks. The communication unit 316 associated with the UE 102 provides the communication interface between the UE 102 and the MCPTT server 108.

The FIG. 3b shows example units of the IMS server 106 but it is to be understood that other embodiments are not limited thereon. In other embodiments, the IMS server 106 may include less or more number of units. Further, the labels or names of the units are used only for illustrative purpose and does not limit the scope of the invention. One or more units can be combined together to perform same or substantially similar function in the IMS server 106.

FIG. 4 is a flow diagram illustrating a method 400 for performing (e.g., simultaneously) the IMS Authentication (Auth) and the MCPTT Authentication (Auth) using the UE 102, according to an embodiment as disclosed herein. At step 402, the method 400 includes sending a REGISTER request message to an IMS server 106. In an embodiment, the method 400 allows the controller unit 302 to send the REGISTER request message to an IMS server 106. The REGISTER request message can include, for example, the IMSI, the IMPU, the IMPI, capability of the UE 102, the IMEI, and the CSG cell ID, or combination of same.

At step 404, the method 400 includes receiving an IMS authentication challenge from the IMS server 106, where the IMS authentication challenge includes an IMS authentication parameter and a MCPTT authentication challenge. The IMS authentication parameter can include, for example, a RAND, AUTN and MCPTT authentication indication. In an embodiment, the method 400 allows the controller unit 302 to receive an IMS authentication challenge from the IMS server 106, where the IMS authentication challenge includes an IMS authentication parameter and a MCPTT authentication challenge.

At step 406, the method 400 includes verifying the IMS authentication challenge. In an embodiment, the method 400 allows the controller unit 302 to verify the IMS authentication challenge.

At step 408, the method 400 includes sending a REGISTER response message to the IMS server 106, where the REGISTER response message can include the IMS authentication response to authenticate the UE 102 at the IMS server 106 and the MCPTT authentication response to authenticate the UE 102 at the MCPTT server 108. In an embodiment, the method 400 allows the controller unit 302 to send the REGISTER response message to the IMS server 106, where the REGISTER response message can include the IMS authentication response to authenticate the UE 102 at the IMS server 106 and a MCPTT authentication response to authenticate the UE 102 at the MCPTT server 108.

The various actions, acts, blocks, steps, or the like in the methods 400 may be performed in the order presented, in a different order or simultaneously. Further, in some embodiments, some of the actions, acts, blocks, steps, or the like may be omitted, added, modified, skipped, or the like without departing from the scope of the invention FIG. 5 is a flow diagram illustrating a method 500 for performing the IMS Auth and the MCPTT Auth in sequence/ MCPTT Auth performed after successful authentication of the IMS Auth using the UE 102, according to an embodiment as disclosed herein. At step 502, the method 500 includes sending the REGISTER request message to the IMS server 106. In an embodiment, the method 400 allows the controller unit 302 to send the REGISTER request message to the IMS server 106. The REGISTER request message can include, for example, the IMSI, the IMPU, the IMPI, capability of the UE 102, the IMEI, and the CSG cell ID, or combination of same. The REGISTER request message can be for example, an INVITE, (group affiliation, subscribe IMPU).

At step 504, the method 500 includes receiving the IMS authentication challenge from the IMS server 106, where the IMS authentication challenge includes the IMS authentication parameter and the MCPTT authentication challenge. In an embodiment, the method 500 allows the controller unit 302 to receive the IMS authentication challenge from the IMS server 106, where the IMS authentication challenge includes the IMS authentication parameter and the MCPTT authentication challenge.

At step 506, the method 500 includes verifying the IMS authentication challenge. In an embodiment, the method 500 allows the controller unit 302 to verify the IMS authentication challenge.

At step 508, the method 500 includes sending the REGISTER response message to the IMS server 106, where the REGISTER response message includes an IMS authentication response to authenticate the UE 102 at the IMS server 106. In an embodiment, the method 500 allows the controller unit 302 to send the REGISTER response message to the IMS server 106, where the REGISTER response message includes an IMS authentication response to authenticate the UE 102 at the IMS server 106.

The various actions, acts, blocks, steps, or the like in the methods 500 may be performed in the order presented, in a different order or simultaneously. Further, in some embodiments, some of the actions, acts, blocks, steps, or the like may be omitted, added, modified, skipped, or the like without departing from the scope of the invention.

FIG. 6 is a flow diagram illustrating a method 600 for performing (e.g., simultaneously) the IMS Authentication (Auth) and the MCPTT Authentication (Auth) by an IMS server 106, according to an embodiment as disclosed herein. At step 602, the method 600 includes receiving the REGISTER request message from the UE 102. In an embodiment, the method 600 allows the controller unit 312 to receive the REGISTER request message from the UE 1021n an embodiment the IMS server 106 includes the P-CSCF 1061 and S-CSCF 1062.

At step 604, the method 600 includes sending the IMS authentication challenge to the UE 102, where the IMS authentication challenge includes an IMS authentication parameter and the MCPTT authentication challenge. In an embodiment, the method 600 allows the controller unit 312 to send the IMS authentication challenge to the UE 102. At step 606, the method 600 includes receiving the REGISTER response message from the UE 102, where the REGISTER response message includes an IMS authentication response to authenticate the UE 102 at the IMS server and a MCPTT authentication response to authenticate the UE 102 at the MCPTT server 108. In an embodiment, the method 600 allows the controller unit 312 to receive the REGISTER response message from the UE 102.

At step 608, the method 600 includes verifying the UE 102 based on the IMS authentication response. In an embodiment, the method 600 allows the controller unit 312 to verify the UE 102 based on the IMS authentication response. At step 610, the method 600 includes sending the MCPTT authentication response to the MCPTT server 108. In an embodiment, the method 600 allows the controller unit 312 to send the MCPTT authentication response to the MCPTT server 108.

At step 612, the method 600 includes receiving the MCPTT success message from the MCPTT server 108. In an embodiment, the method 600 allows the controller unit 312 to receive the MCPTT success message from the MCPTT server 108.

At step 614, the method 600 includes registering the UE 102 based on the MCPTT success message. In an embodiment, the method 600 allows the controller unit 312 to register the UE 102 based on the MCPTT success message.

At step 616, the method 600 includes sending the IMS authentication success message to the UE 102. In an embodiment, the method 600 allows the controller unit 312 to send the IMS authentication success message to the UE 102.

The various actions, acts, blocks, steps, or the like in the methods 600 may be performed in the order presented, in a different order or simultaneously. Further, in some embodiments, some of the actions, acts, blocks, steps, or the like may be omitted, added, modified, skipped, or the like without departing from the scope of the invention.

FIG. 7 is a flow diagram illustrating a method 700 for performing the IMS Auth and the MCPTT Auth in sequence/MCPTT Auth performed after successful authentication of IMS Auth by an IMS server 106 through the controller unit 312, according to an embodiment as disclosed herein. At step 702, the method 700 includes receiving a REGISTER request message from the UE 102. At step 704, the method 700 includes sending the IMS authentication challenge to the UE 102, where the IMS authentication challenge includes the IMS authentication parameter and the MCPTT authentication indication.

At step 706, the method 700 includes receiving a REGISTER response message from the UE 102, where the REGISTER response message includes the IMS authentication response to authenticate the UE 102 at the IMS server 106. At step 708, the method 700 includes verifying the UE 102 based on the IMS authentication response. At step 710, the method 700 includes sending the IMS authentication success message response from the UE 102.

At step 712, the method 700 includes receiving the MCPTT authentication challenge from the MCPTT server 108. At step 714, the method 700 includes sending an IMS authentication challenge to the UE 102, where the IMS authentication challenge comprises the MCPTT authentication challenge. At step 716, the method 700 includes receiving the REGISTER response message from the UE 102, where the REGISTER response message includes the MCPTT authentication response to authenticate the UE 102 at the MCPTT server 108.

The various actions, acts, blocks, steps, or the like in the method 700 may be performed in the order presented, in a different order or simultaneously. Further, in some embodiments, some of the actions, acts, blocks, steps, or the like may be omitted, added, modified, skipped, or the like without departing from the scope of the invention.

FIG. 8 illustrates a sequence diagram performing IMS Authentication and MCPTT Authentication sequentially, according to an embodiment as disclosed herein. In an embodiment, the signaling sequence depicts communication between the UE 102, subscriber database 104, the IMS server 106 and the MCPTT server 108. In an embodiment, the IMS network associated with the IMS server 106 can determine whether the UE 102 requires the MCPTT Authentication (application level authentication), based on the one or more parameters, for example IMEI of the UE 102 or the IMSI (shared UE 102), an indication from HSS (Operator configuration of the UE 102), the IMPI associated with the UE 102, the IMPU (IMS subscription) associated with the UE 102 and the MCPTT ID or MCPTT service domain associated with the UE 102.

Once the UE 102 has obtained IP connectivity (LTE access), the UE 102 can therefore perform the IM registration (for MCPTT service). For this purpose the UE 102 sends (802) the register information flow (REGISTER request message), associated with the UE 102, to the P-CSCF 1061. In an embodiment the UE 102 can include the IMPI and the IMPUs, where one of the IMPU is assigned to the MCPTT service and included in the REGISTER message request. In an embodiment, the REGISTER message request associated with the UE 102 can include the identity corresponding to the MCPTT service (IMPU, MCPTT ID, User ID and MCPTT user ID).

Upon receipt of the register information flow, the P-CSCF 1061 examines the "home domain name" (HSS 104) to discover the entry point to the home network (i.e. Interrogating CSCF (I-CSCF)). The P-CSCF 1061 then sends (804) the Register information flow to the S-CSCF 1062 (the Register information flow can include, for example P-CSCF 1061 address or name, Public User Identity, Private User Identity, P-CSCF 1061 network identifier and IP address corresponding to the UE 102). If the IMPU (corresponding to the MCPTT client unit 308) is not registered at the S-CSCF 1062, the S-CSCF 1062 can set the registration flag (806) at the HSS 104 to initial registration pending to handle UE 102 terminated calls while the initial registration is in progress and not successfully completed. The registration flag is stored in the HSS 104 together with the S-CSCF 1062 name and user identity, and is used to indicate whether a particular IMPU of the UE 102 is unregistered or registered at a particular S-CSCF 1062 or if the initial registration at a particular S-CSCF 1062 is pending. The registration flag is set by the S-CSCF 1062, sending a Cx-Put to the HSS 104.

In addition, if the S-CSCF 1062 has no valid Authentication Vector (AV) then the S-CSCF 1062 can send a request for AV(s) to the HSS. Upon receipt of a request from the S-CSCF 1062, the HSS 104 sends an ordered array of "n" authentication vectors to the S-CSCF 1062. The HSS 104 identifies whether the MCPTT authentication is also required for registration and if required, indicates the same to the S-CSCF 1062.

In an embodiment, each authentication vector can include one or more following components: a random number RAND, an expected response XRES, a cipher key CK, an integrity key (IK) and an authentication token AUTN for IM authentication. Each authentication vector is good for one IM registration authentication and key agreement between the S-CSCF 1062 and a user of the IMS service.

The S-CSCF 1062 thereon sends (808) a SIP 4xxAuth_Challenge (the IMS authentication challenge) to the P-CSCF 1061 i.e. an authentication challenge towards the UE 102 including the challenge RAND, the authentication token AUTN. It also includes the integrity key IK and the cipher key CK for the P-CSCF 1061. If indicated by HSS that MCPTT authentication is required (MCPTT authentication challenge), then the S-CSCF 1062, includes Multiple Auth Required indicator (IE) in the message (4xxAuth_Challenge). When the P-CSCF 1061 receives the message, it stores the key(s) and extract the information associated with the message and forward (810) the message to the UE 102.

The UE 102 upon receiving the challenge, the UE 102 takes the AUTN, which includes a MAC and calculates the XMAC and verifies (812) that XMAC=MAC. If the check is successful the UE 102 uses RES and some other parameters to calculate an authentication response. The UE 102 may enable the Authentication response into the Authorization header and transmits (814) to the registrar (P-CSCF 1061). The P-CSCF 1061 then forwards (816) the authentication response (REGISTER response message) received from the UE 102 to the S-CSCF 1062. The S-CSCF 1062 upon receiving the message (REGISTER response message) containing the response, the S-CSCF 1062 retrieves the active XRES for that UE 102 and uses this to check (818) the authentication response sent by the UE 102. If the check is successful then the UE 102 is authenticated for the IM. However, to register the IMPU corresponding to the MCPTT service of the UE 102, another authentication with the MCPTT server 108 (MCPTT Application Server (AS)) needs to be performed. If the IM auth has been successfully authenticated, the S-CSCF 1062 can send (820) a SIP 2xxAuth_OK message (IMS authentication success message) to the P-CSCF 1061 indicating that the registration was successful. The P-CSCF 1061 forwards (822) the SIP 2xxAuth_OK (IMS authentication success message) towards the UE 102.

The UE 102 upon receiving the SIP 2xxAuth_OK message thereon initiates (sending) (824) the Register (analogous to register request message), message carrying the IMPU corresponding to the MCPTT service. The UE 102 can explicitly include the indication (MCPTT authentication indication) that this register message is to perform MCPTT authentication. The P-CSCF 1061, upon receipt of the register message, may forward (826) to the S-CSCF 1062. The S-CSCF 1062 then forwards (828) register message to the MCPTT server 108. The S-CSCF 1062 identifies the MCPTT using one or more of the following: using the MCPTT IMPU, MCPTT User ID, Preconfigured in the HSS and HSS, DNS resolution of FQDN provided by the UE 102 or the like. The MCPTT server 108 contacts the HSS or MCPTT subscriber database to obtain (830) Authentication Vector (AV) for SIP Digest based authentication. The HSS or MCPTT database sends one SD-AV to the MCPTT server 108. The SD-AV consists of the QoP (quality of protection) value, the authentication instructions, realm, and a hash called H (A1) of the IMPI, realm, and password.

The MCPTT server 108 can generate a random nonce, stores 5 H(A1) and the nonce against the IMPI, and then sends (832), through the S-CSCF 1062, a SIP 401 Auth_Challenge (a MCPTT authentication challenge) i.e., an authentication challenge towards the UE 102 including the nonce. It also includes the realm, QoP and instruction parameters. The S-CSCF 1062 forwards (834) the SIP 4xxAuth_Challenge message (a MCPTT authentication challenge) towards the P-CSCF 1061. The P-CSCF 1061 forwards (836) the SIP 4xxAuth_Challenge message towards the UE 102. Upon receiving the challenge (a MCPTT authentication challenge), the UE 102 generates a cnonce. It then uses the cnonce as well as parameters such as nonce and QoP to calculate (838) an authentication response. The authentication response and other parameters are put into the Authorization header and sent (840), through the IMS server 106, back towards the MCPTT server 108.

The P-CSCF 1061 forwards (842) the authentication response to the S-CSCF 1062. The S-CSCF 1062 forwards (844) the authentication response to the MCPTT server 108. The MCPTT server upon receiving the message containing the response (MCPTT authentication challenge), the MCPTT server 108 calculates the expected response using the previously stored H(A1) and stored nonce together with other parameters contained and uses this to check (846) against the response sent by the UE 102. If the check is successful the UE 102 is thus authenticated for the MCPTT service.

If the UE 102 has been successfully authenticated, the MCPTT server 108 sends (848) a SIP 2xxAuth_OK message to the S-CSCF $106_2$ indicating that the authentication was successful. The 2xxAuth_OK message contains the Authentication-Info header with a response digest. The response digest allows the UE 102 to authenticate the MCPTT server 108. Further the MCPTT server 108 indicates or includes the authenticated MCPTT ID, for the S-CSCF $106_2$ to bind with the IMPU, if IMPU and the MCPTT ID are different. The S-CSCF $106_2$ upon receiving the message containing the response, the IMPU is registered in the S-CSCF $106_2$. If the IMPU was not currently registered, the S-CSCF $106_2$ can send (850) a Cx-Put to update the registration-flag to "registered". In an embodiment, either IMPU or MCPTT ID or both can be used to identify the UE 102, in subsequent service interactions e.g. calls, MCPTT, like so.

The S-CSCF $106_2$ forwards (852) the SIP 2xxAuth_OK towards the P-CSCF $106_1$. The P-CSCF $106_1$ associates the UE's packet source IP address along with the "sent-by" parameter of the via header of the REGISTER message with the IMPI and all the successfully registered IMPUs (which includes the MCPTT IDs) related to that IMPI. The P-CSCF 106₁ thereon forwards (854) the SIP 2xxAUTH_OK towards the UE 102. The UE 102 upon receiving the message, the UE 102 can calculate (856) the expected response from the MCPTT server 108. To authenticate the MCPTT server 108, the UE 102 can compare its expected response to the response provided by the MCPTT server 108.

In an embodiment, the signaling message (as indicated at 802) to the signaling message (as indicated at 824) illustrates MCPTT UE 102 authentication procedure using IMS AKA. IMS AKA procedure is performed. The signaling message (as indicated at 828) to the signaling message (as indicated at 830) can be a third party registration procedure, performed between the IMS Core and the MCPTT server 108 after successful IMS authentication procedures.

In an embodiment, the signaling message (832) to the signaling message (856) illustrates MCPTT user authentication procedure, performed using Non-registration Messages between the UE and the MCPTT Server. SIP digest mechanism used and S-CSCF 1062 functions are performed by the MCPTT server 108. If the authentication is successful, the MCPTT server 108 flags or marks that the MCPTT user ID is authenticated. For further messages after successful authentication, the MCPTT server 108 checks whether the user identity is authenticated or not, before processing the message.

FIG. 9 illustrates another sequence diagram performing IMS Authentication and MCPTT Authentication together, according to an embodiment as disclosed herein. In an embodiment, the signaling sequence depicts communication between the UE 102, subscriber database 104, the IMS server 106 and the MCPTT server 108. In an embodiment, the IMS network associated with the IMS server 106 can determine whether the UE 102 requires the MCPTT Authentication (application level authentication), based on the one or more parameters, for example IMEI of the UE 102 or the IMSI (shared UE 102), an Indication from HSS (Operator configuration of the UE 102), the IMPI associated with the UE 102, the IMPU (IMS subscription) associated with the UE 102 and the MCPTT ID or MCPTT service domain associated with the UE 102.

The UE 102 obtaining the IP connectivity (LTE access), can therefore perform the IM registration (for MCPTT service), upon which the UE 102 sends (902) the register information flow (REGISTER request message), associated with the UE 102, to the P-CSCF 1061. In an embodiment the UE 102 can include the IMPI and the IMPUs, where one of the IMPU is assigned to the MCPTT service and included in the REGISTER message request. In an embodiment, the REGISTER message request associated with the UE 102 can include the identity corresponding to the MCPTT service (IMPU, MCPTT ID, User ID and MCPTT user ID). The P-CSCF 1061 upon receipt of the register information flow examines the "home domain name" (HSS 104) to discover the entry point to the home network (i.e. Interrogating CSCF (I-CSCF)). The P-CSCF 1061 then sends (904) the Register information flow to the S-CSCF 1062 (the Register information flow can include, for example P-CSCF 1061 address or name, Public User Identity, Private User Identity, P-CSCF 1061 network identifier and IP address corresponding to the UE 102).

If the IMPU (corresponding to the MCPTT client unit 308) is not registered at the S-CSCF 1062, the S-CSCF 1062 can set the registration flag (906) at the HSS to initial registration pending in order to handle UE 102 terminated calls while the initial registration is in progress and not successfully completed. The registration flag is stored in the HSS 104 together with the S-CSCF 1062 name and user identity, and is used to indicate whether a particular IMPU of the UE 102 is unregistered or registered at a particular S-CSCF 1062 or if the initial registration at a particular S-CSCF 1062 is pending. The registration flag is set by the S-CSCF 1062, sending a Cx-Put to the HSS 104. In addition, if the S-CSCF 1062 has no valid Authentication Vector (AV) then the S-CSCF 1062 can send a request for AV(s) to the HSS. Upon receipt of a request from the S-CSCF 1062, the HSS 104 sends an ordered array of "n" authentication vectors to the S-CSCF 1062. The HSS 104 identifies whether the MCPTT authentication is also required for registration and if required, indicates the same to the S-CSCF 1062.

In an embodiment, each authentication vector (AV) can include one or more following components: a random number RAND, an expected response XRES, a cipher key CK, an integrity key IK and an authentication token AUTN for IM authentication. Each authentication vector is good for one IM registration authentication and key agreement between the S-CSCF 1062 and a user of the IMS service.

The S-CSCF 1062 on indication that MCPTT authentication is required, forwards (908) the register message to the MCPTT server 108. The S-CSCF 1062 identifies the MCPTT using one or more of the following: using the MCPTT IMPU, MCPTT User ID, Preconfigured in the HSS and the HSS 104, DNS resolution of FQDN provided by the UE or the like. The MCPTT server 108 upon receipt of a request from the S-CSCF 1062 can decide whether MCPTT authentication is required in addition to HSS. In an embodiment, either HSS 104 decides or the MCPTT server 108 decides whether MCPTT authentication is required. Thus, the decision can be based on the one or more the service provider configuration, based on MCPTT User ID and the sharable UE 102. If the decision is to authenticate the UE 102, then MCPTT server 108 contacts the HSS 104 or MCPTT subscriber database to obtain (910) authentication vector for SIP Digest based authentication. The HSS 104 or the MCPTT database sends one SD-AV to the MCPTT server 108. The SD-AV consists of the QoP (quality of protection) value, the authentication instruction, realm, and a hash, called 10 H (A1), of the IMPI, realm, and password.

The MCPTT server 108 generates a random nonce, stores H (A1) and the nonce against the IMPI, and then sends (912) a SIP 401 (i.e, 4XX) Auth_Challenge i.e., an authentication challenge, through the S-CSCF 1062, towards the UE 102 including the nonce. It also includes the realm, QoP and instruction parameters. The MCPTT includes Multiple Auth Required indication or (IE) in the SIP 401 Auth_Challenge message. The S-CSCF 1062 sends (914) the received SIP 4xxAuth_Challenge from the MCPTT server 108 along with other parameters i.e. an authentication challenge, through the P-CSCF 1061, towards the UE 102 including the challenge RAND, the authentication token AUTN. It also includes the integrity key IK and the cipher key CK for the P-CSCF 1061. If indicated by HSS 104 that the MCPTT authentication is required, then the S-CSCF 1062, includes Multiple Auth Required indicator (or IE) in the message (4xxAuth_Challenge). When the P-CSCF 1061 receives the message from the S-CSCF 1062, it stores the key(s) and removes that information and forwards (916) the message to the UE 102.

The UE 102 upon receiving the challenge takes the AUTN which includes a MAC. The UE 102 calculates (e.g., verifies) (918) the XMAC and checks that XMAC=MAC. If the check is successful the UE 102 uses RES and some other parameters to calculate an authentication response (for IM authentication). Further, the UE 102 generates a cnonce (AKA RES). It then uses the cnonce as well as the parameters such as nonce and QoP to calculate an authentication response (SD response) (for MCPTT authentication). The authentication responses and other parameters are put into the Authorization header (REGISTER response message) and transmitted (920) through the IMS server 106, back towards the registrar and MCPTT server 108.

The P-CSCF 1061 forwards (922) the authentication response received from the UE 102 to the S-CSCF 1062. The S-CSCF 1062 upon receiving the message containing the response, the S-CSCF 1062 retrieves the active XRES for that user (of the UE 102) and uses this to check (verifies) (924) the authentication response sent by the UE 102. If the check is successful then the UE 102 has been authenticated for IM. However, to register the IMPU corresponding to the MCPTT service of the UE 102, another check with the MCPTT server 108 (MCPTT application server) needs to be performed. If the IM authentication is successfully authenticated, the S-CSCF 1062 forwards (926) the authentication response (with relevant MCPTT authentication challenge parameters) to the MCPTT server 108.

The MCPTT server 108 upon receiving the message containing the response verifies (928) the MCPTT_Auth response using the previously stored H (A1) and stored nonce together with other parameters contained and uses this to check against the response sent by the UE 102. If the check is successful then the UE 102 is authenticated for MCPTT service. If the UE 102 is successfully authenticated, the MCPTT server 108 sends (930) a SIP 2xxAuth_OK message to the S-CSCF 1062 indicating that the authentication was successful. The 2xxAuth_OK message contains the Authentication-Info header with a response digest. The response digest allows the UE 102 to authenticate the MCPTT server 108. Further the MCPTT server 108 includes the authenticated MCPTT ID, for the S-CSCF 1062 to bind with the IMPU, if IMPU and the MCPTT ID are different. Upon receiving the message containing the response, the IMPU is registered in the S-CSCF 1062. If the IMPU was not currently registered, the S-CSCF 1062 can send (932) a Cx-Put to update the registration-flag to "registered".

The S-CSCF 1062 forwards (934) the SIP 2xxAuth_OK towards the P-CSCF 1061. The P-CSCF 1061 associates the UE's packet source IP address along with the "sent-by" parameter of the Via header of the REGISTER message with the IMPI and all the successfully registered IMPUs (which includes the MCPTT IDs) related to that IMPI. Further, the P-CSCF 1061 forwards (936) the SIP 2xxAUTH_OK towards the UE 102.

The UE 102 upon receiving the message verifies (938) the expected response from the MCPTT server 108. To authenticate the MCPTT server 108, the UE 102 compares its expected response to the response provided by the MCPTT server 108.

FIG. 10 illustrates yet another sequence diagram performing MCPTT Authentication after successful IMS Authentication, according to an embodiment as disclosed herein. In an embodiment, the signaling sequence depicts communication between the UE 102, subscriber database 104, the IMS server 106 and the MCPTT server 108. In an embodiment, the IMS network associated with the IMS server 106 can determine whether the UE 102 requires the MCPTT Authentication (application level authentication), based on the one or more parameters, for example IMEI of the UE 102 or the IMSI (shared UE 102), an Indication from HSS (Operator configuration of the UE 102), the IMPI associated with the UE 102, the IMPU (IMS subscription) associated with the UE 102 and the MCPTT ID or MCPTT service domain associated with the UE 102.

Once the UE 102 has obtained IP connectivity (LTE access), the UE 102 can therefore perform the IM registration (for MCPTT service). For this purpose the UE 102 sends (1002) the register information flow (REGISTER request message), associated with the UE 102, to the P-CSCF 1061. In an embodiment the UE 102 can include the IMPI and the IMPUs, where one of the IMPU is assigned to the MCPTT service and included in the REGISTER message request. In an embodiment, the REGISTER message request associated with the UE 102 can include the identity corresponding to the MCPTT service (IMPU, MCPTT ID, User ID and MCPTT user ID). Upon receipt of the register information flow, the P-CSCF 1061 examines the "home domain name" (HSS 104) to discover the entry point to the home network (i.e. Interrogating CSCF (I-CSCF)). The P-CSCF 1061 then sends (1004) the Register information flow to the S-CSCF 1062 (the Register information flow can include, for example P-CSCF 1061 address or name, Public User Identity, Private User Identity, P-CSCF 1061 network identifier and IP address corresponding to the UE 102).

If the IMPU (corresponding to the MCPTT client unit 308) is not registered at the S-CSCF 1062, the S-CSCF 1062 can set (1006) the registration flag at the HSS 104 to initial registration pending to handle the UE 102 terminated calls while the initial registration is in progress and not successfully completed. The registration flag is stored in the HSS 104 together with the S-CSCF 1062 name and user identity, and is used to indicate whether a particular IMPU of the UE 102 is unregistered or registered at a particular S-CSCF 1062 or if the initial registration at a particular S-CSCF 1062 is pending. The registration flag is set by the S-CSCF 1062, sending a Cx-Put to the HSS 104.

In addition, if the S-CSCF 1062 has no valid Authentication Vector (AV) then the S-CSCF 1062 can send a request for AV(s) to the HSS. Upon receipt of a request from the S-CSCF 1062, the HSS 104 sends an ordered array of "n" authentication vectors to the S-CSCF 1062. The HSS 104 identifies whether the MCPTT authentication is also required for registration and if required, indicates the same to the S-CSCF 1062.

In an embodiment, each authentication vector can include one or more following components: a random number RAND, an expected response XRES, a cipher key CK, an integrity key IK and an authentication token AUTN for IM authentication. Each authentication vector is good for one IM registration authentication and key agreement between the S-CSCF 1062 and a user of the IMS service.

The S-CSCF 1062 sends (1008) a SIP 4xxAuth_Challenge (the IMS authentication challenge) to the P-CSCF 1061 i.e. an authentication challenge towards the UE 102 including the challenge RAND, the authentication token AUTN. It also includes the integrity key IK and the cipher key CK for the P-CSCF 1061. If indicated by HSS that MCPTT authentication is required (MCPTT authentication challenge), then the S-CSCF 1062, includes Multiple Auth Required indicator (IE) in the message (4xxAuth_Challenge). When the P-CSCF 1061 receives the message, it stores the key(s) and extract the information associated with the message and forwards (1010) the message to the UE 102.

Upon receiving the challenge, the UE 102 takes the AUTN, which includes a MAC. The UE 102 verifies (1012) the XMAC and checks that XMAC=MAC. If the check is successful the UE 102 uses RES and some other parameters to calculate an authentication response.

The authentication response is put into the Authorization header (the REGISTER response message) and sent (1014) to the registrar. The P-CSCF 1061 then forwards (1016) the authentication response (REGISTER response message) received from the UE 102 to the S-CSCF 1062. Upon receiving the message (REGISTER response message) containing the response, the S-CSCF 1062 retrieves (1018) the active XRES for that UE 102 and uses this to check the authentication response sent by the UE 102. If the check is successful then the UE 102 is authenticated for IM. However, to register the IMPU corresponding to the MCPTT service of the UE 102, another authentication with the MCPTT server 108 (i.e, MCPTT Application Server (AS)) needs to be performed.

If the IM authentication is successfully authenticated, the S-CSCF 1062 thereon forwards (1020) the authentication response (with relevant MCPTT authentication parameters (MCPTT ID or MCPTT-IMPU)) to the MCPTT server 108. The S-CSCF 1062 identifies the MCPTT using one or more of the following: using the MCPTT IMPU, MCPTT user ID, Preconfigured in the HSS and HSS 104, DNS resolution of FQDN provided by the UE 102 or the like. Upon receipt of a request from the S-CSCF 1062, the MCPTT server 108 contacts the HSS 104 or MCPTT subscriber database to obtain (1022) authentication vector for SIP Digest based authentication.

The HSS 104 or MCPTT database sends one SD-AV to the MCPTT server 108. The SD-AV consists of the QoP (quality of protection) value, the authentication instructions, realm, and a hash, called H (A1), of the IMPI, realm, and password. The MCPTT server 108 generates a random nonce, stores H (A1) and the nonce against the IMPI, and then sends (1024) a SIP 401 Auth_Challenge i.e., an authentication challenge towards, through the S-CSCF 1062, the UE 102 including the nonce. It also includes the realm, QoP and instruction parameters. In an embodiment, the MCPTT server 108 includes an indication that the authentication challenge is for MCPTT authentication.

The S-CSCF 1062 forwards (1026) the SIP 4xxAuth_Challenge message (a MCPTT authentication challenge) towards the P-CSCF 1061. The P-CSCF 1061 thereon forwards (1028) the SIP 4xxAuth_Challenge message towards the UE 102.

The UE 102 upon receiving the challenge (a MCPTT authentication challenge), generates a cnonce. It then uses the cnonce as well as parameters such as nonce and QoP to calculate (1030) an authentication response. The UE 102 identifies that the auth challenge is for MCPTT authentication and at least one of the indication from the MCPTT server 108 and the realm. The authentication response and other parameters are put into the Authorization header and sent (1032), through the IMS serve 106, back towards the MCPTT server 108.

The P-CSCF 1061 forwards (1034) the authentication response to the S-CSCF 1062. The S-CSCF 1062 forwards (1036) the authentication response to the MCPTT server 108.

Upon receiving the message containing the response (MCPTT authentication challenge), the MCPTT server 108 verifies (1038) the MCPPT_Auth response using the previously stored H(A1) and stored nonce together with other parameters contained and uses this to check against the response sent by the UE 102. If the check is successful then the UE 102 has been authenticated for MCPTT service.

If the UE 102 has been successfully authenticated, the MCPTT server 108 sends (1040) a SIP 2xxAuth_OK message to the S-CSCF 106₂ indicating that the authentication was successful. The 2xxAuth_OK message contains the Authentication-Info header with a response digest. The response digest allows the UE 102 to authenticate the MCPTT server 108. Further the MCPTT server 108 indicates or includes the authenticated MCPTT ID, for the S-CSCF 106₂ to bind with the IMPU, if IMPU and the MCPTT ID are different. Upon receiving the message containing the response, the IMPU is registered in the S-CSCF 106₂. If the IMPU was not currently registered, the S-CSCF 106₂ can send (1042) a Cx-Put to update the registration-flag to "registered".

The S-CSCF 106₂ forwards (1044) the SIP 2xxAuth_OK towards the P-CSCF 106₁. The P-CSCF 106₁ associates the UE's packet source IP address along with the "sent-by" parameter of the via header of the REGISTER message with the IMPI and all the successfully registered IMPUs (which includes the MCPTT IDs) related to that IMPI. The P-CSCF 106 ¬1 forwards (1046) the SIP 2xxAUTH_OK towards the UE 102.

Upon receiving the message, the UE 102 verifies (1048) the expected response from the MCPTT server 108. To authenticate the MCPTT server 108, the UE 102 can compare its expected response to the response provided by the MCPTT server 108.

In an embodiment, the UE 102 behavior is that, when the network indicates multiple authentications need to be performed; thereon the UE 102 performs the authentication procedure in sequence. The sequence of the authentication procedure is indicated by the network during registration request or pre-configured in the UE.

In an embodiment, the signaling messages 1030 to 1042 (MCPTT authentication) can be performed directly between MCPTT server 108 and UE 102 excluding going through S-CSCF 1062 and P-CSCF 1061. After successful authentication, MCPTT server 108 indicates that the IMPU/MCPTT ID is authenticated and request SIP registration for the same. This alternative of performing (MCPTT authentication) directly between MCPTT server 108 and UE 102 is application for other mechanisms specified in this application.

In an embodiment, MCPTT authentication happening before SIP/IMS authentication (for e.g. for Trusted Node Authentication (TNA) mechanism using token) and it is applicable to all other alternatives specified in this application. The registration to the service is performed after successful authentication of both procedures.

In an embodiment, the SIP authentication can be: IMS-AKA, SIP digest authentication, TNA mechanism. In an embodiment, MCPTT authentication can be at least one of: IMS-AKA, SIP digest authentication, TNA mechanism. Any one IMS-AKA, SIP digest authentication, TNA mechanism is performed by the MCPTT capable UE 102 with the SIP core or MCPTT service domains to gain IMS and MCPTT service access.

FIG. 11 illustrates a sequence diagram describing an example of call flow for MCPTT service authentication, according to an embodiment as disclosed herein. In an embodiment consider a scenario where a separate authentication process independently from a SIP registration phases is performed, for example if the SIP core 1106 is outside the domain of the MCPTT server 108. Other alternatives are possible, such as authenticating the user within the SIP registration phase.

Initially the MCPTT user performs (1102) the user authentication procedure and acquires an access token, wherein the MCPTT user supplies the user credentials (e.g. biometrics, secure ID, username or password) for verification with the identity management server 108. The signaling user agent establishes (1104) a secure connection to the SIP core 1106 for the purpose of SIP level authentication and registration. Further, the signaling user agent completes (1106) the SIP level registration with the SIP core (and an optional third-party registration with the MCPTT server 108). The MCPTT client 308 performs the MCPTT service authorization for the user.

FIG. 12 illustrates a sequence diagram describing an example for performing MCPTT user authentication and registration using the token according to an embodiment as disclosed herein. The user powers-on the UE 102 thereon the UE 102 performs (1202) LTE attach procedure (LTE authentication) and obtains the IP connectivity. The user enables the MCPTT client 308. The MCPTT client 308 accesses a Uniform Resource Identifier (URI) to the Identity Management (IM) function to initiate a Hypertext Transfer Protocol over the Transport Layer Security (HTTPS) (1204) connection to the IM function. The TLS connection provides one-way authentication of the server based on the server certificate. The HTTP-1 interface is used between the MCPTT Client 308 and the Identity Management server 1108.

The MCPTT client 308 begins (1206) the user authorization procedure by sending an Authentication Request (IMPU, MCPTT user identity, user credentials) message to the Identity Management function. The IMPU is taken from the ISIM in the UE 102. The MCPTT user identity may be obtained from the user input or via other methods. The user provides the MCPTT user authentication credentials (e.g. biometrics, password, etc.) for verification with the Identity Management function. The Identity Management function authenticates the user using the MCPTT user identity and MCPTT user authentication credentials. If the authentication is successful, the Identity Management function generates (1208) Token based on the IMPU and the MCPTT user identity. The token is encoded with the associated authorization information, including the MCPTT user identity and IMPU assigned to the user and the authorization token scope. The Identity Management function responds with an Authentication Response message to the UE, which includes the access token for service authorization with the MCPTT server.

The UE 102 initiates (1210) IMS registration procedure and use IMS AKA for signaling plane authentication. IMS AKA run is performed as illustrated. In addition, the UE 102 includes the access token for MCPTT user authentication, along with IMS registration message. The S-CSCF 1062 acknowledges (1212) with an OK message and the OK message is forwarded to the client.

If the IMS AKA is successful, the S-CSCF 1062 performs the third party registration with the MCPTT server 108. The S-CSCF 1062 sends (1214) a Register (IMPU, Token) message to the MCPTT server 108. The MCPTT server 108 verifies (1216) the token. If the token is valid, the MCPTT server 108 trust the MCPTT user identified by the MCPTT user ID is a valid user and the server stores the relationship between the IMPU and the MCPTT user identity.

The MCPTT server 108 acknowledges, with an OK message, and is signaled (1218) to, through the S-CSCF 1062 and the P-CSCF 1061, the UE 102.

The UE 102 may receive the MCPTT service authorization (1220) signaling from the MCPTT server 108 thereof the UE 102 can be authorized to utilize the MCPPT service. Alternatively, if the verification (as indicated at step 1216) fails, then the MCPTT server indicates third party registration failure and then the IMS network indicate the MCPTT service authorization failure to the UE appropriately.

FIG. 12*b* is a flow diagram illustrating a method 1200 for MCPTT service registration, according to an embodiment as disclosed herein. At step 1202, the method 1200 includes performing the LTE and EPS attach procedure in order to obtain the IP connectivity. In an embodiment, the method 1200 allows the controller unit 302 to perform the LTE and EPS attach procedure in order to obtain the IP connectivity.

At step 1204, the method 1200 includes performing MCPTT user authentication. In an embodiment, the method 1200 allows the controller unit 302 to perform the MCPTT user authentication.

The MCPTT user authentication may include enabling the MCPPT client 308 to access the URI to the IM function for initiating the HTTPS connection to the IM function. The TLS connection provides one-way authentication of the server based on the server certificate. The HTTP-1 interface is used between the MCPTT Client 308 and the Identity Management server 1108.

At step 1206, the method 1200 includes performing the SIP registration and authentication. In an embodiment, the method 1200 allows the controller unit 302 to perform the SIP registration and authentication.

The SIP registration and authentication may include sending the IMS registration request using the IMS AKA for the signaling plane authentication. The IMS AKA is illustrated in the FIG. 12*a*. In addition, the UE 102 includes the token for MCPTT user authentication.

At step 1208, the method 1200 includes performing the third party registration. The third party registration is performed with the MCPTT server 108 upon the receipt of token verification, sent from the UE 102, to the MCPTT server 108.

At step 1210, the method 1200 includes performing MCPTT service authentication/authorization. In an embodiment, the method 1200 allows the controller unit 302 to perform MCPTT service authentication.

The SIP registration (at step 1206) and the MCPTT user authentication (at step 1204) may be performed in parallel to the MCPTT authorization.

If the token is available prior to the SIP registration and authentication (at step 1206) thereof the bundled authentication is performed within the SIP registration and authentication therein (at step 1206) and the third party registration (at step 1208).

If the token is unavailable prior to the SIP registration and authentication (at step 1206) thereon the sequence authentication is performed in MCPTT service authorization (at step 1210).

The various actions, acts, blocks, steps, or the like in the methods 1200 may be performed in the order presented, in a different order or simultaneously. Further, in some embodiments, some of the actions, acts, blocks, steps, or the like may be omitted, added, modified, skipped, or the like without departing from the scope of the invention.

FIG. 13 illustrates a computing environment implementing the method for performing multiple authentications within a service registration procedure, according to embodiments as disclosed herein. As depicted in the figure, the computing environment 1302 comprises at least one processing unit 1308 that is equipped with a control unit 1304 and an Arithmetic Logic Unit (ALU) 1306, a memory 1310, a storage unit 1312, plurality of networking devices 1316 and a plurality of Input output (I/O) devices 1314. The processing unit 1308 is responsible for processing the instructions of the schemes. The processing unit 1308 receives commands from the control unit in order to perform its processing. Further, any logical and arithmetic operations involved in the execution of the instructions are computed with the help of the ALU 1306.

The overall computing environment 1302 can be composed of multiple homogeneous or heterogeneous cores, multiple CPUs of different kinds, special media and other accelerators. The processing unit 1308 is responsible for processing the instructions of the schemes. Further, the plurality of processing units 1308 may be located on a single chip or over multiple chips.

The scheme comprising of instructions and codes required for the implementation are stored in either the memory unit 1310 or the storage 1312 or both. At the time of execution, the instructions may be fetched from the corresponding memory 1310 or storage 1312, and executed by the processing unit 1408.

In case of any hardware implementations various networking devices 1316 or external I/O devices 1314 may be connected to the computing environment to support the implementation through the networking unit and the I/O device unit.

The embodiments disclosed herein can be implemented through at least one software program running on at least one hardware device and performing network management functions to control the elements. The elements shown in the FIGS. 1*a* through 13 include blocks which can be at least one of a hardware device, or a combination of hardware device and software units.

The foregoing description of the specific embodiments will so fully reveal the general nature of the embodiments herein that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A method for performing multiple authentications within a service registration procedure by a user equipment (UE), the method comprising:
    receiving, from a session initiation protocol (SIP) core, an authentication challenge;
    verifying the authentication challenge; and
    transmitting, to the SIP core, a first register message including an access token to authenticate the UE in the SIP core and to authenticate the UE in a mission critical push to talk (MCPTT) server,
    wherein a second register message including the access token is transmitted from the SIP Core to the MCPTT server to authenticate the UE in the MCPTT server in case that a successful SIP authentication is performed based on the first register message.

2. The method of claim 1, wherein an IP multimedia public user identity (IMPU) is bound with a MCPTT ID by the MCPTT server when the MCPTT server receives the second register message.

3. The method of claim 1, wherein the first register message and the second register message include a parameter to authenticate the UE in the MCPTT server respectively.

4. A method for performing multiple authentications within a service registration procedure by a session initiation protocol (SIP) core, the method comprising:
    transmitting, to a user equipment (UE), an authentication challenge to be verified the authentication challenge in the UE;
    receiving, from the UE, a first register message including an access token to authenticate the UE in the SIP core and to authenticate the UE in a mission critical push to talk (MCPTT) server; and
    transmitting, to the MCPTT server, a second register message including the access token to authenticate the UE in the MCPTT server in case that a successful SIP authentication is performed based on the first register message.

5. The method of claim 4, wherein an IP multimedia public user identity (IMPU) is bound with a MCPTT ID by the MCPTT server when the MCPTT server receives the second register message.

6. The method claim 4, wherein the first register message and the second register message include a parameter to authenticate the UE in the MCPTT server respectively.

7. A user equipment (UE) for performing multiple authentications within a service registration procedure, the UE comprising:
    a transceiver; and
    a controller coupled with the transceiver and configured to control to:
        receive, from a session initiation protocol (SIP) core, an authentication challenge,
        verify the authentication challenge, and
        transmit, to the SIP core a first register message including an access token to authenticate the UE in the SIP core and to authenticate the UE in a mission critical push to talk (MCPTT) server,
    wherein a second register message including the access token is transmitted from the SIP Core to the MCPTT server to authenticate the UE in the MCPTT server in case that a successful SIP authentication is performed based on the first register message.

8. The UE of claim 7, wherein the first register message and the second register message include a parameter to authenticate the UE in the MCPTT server respectively.

9. A session initiation protocol (SIP) core for performing multiple authentications within a service registration procedure, the SIP core comprising:
    a transceiver; and
    a controller coupled with the transceiver and configured to control to:
        transmit, to a user equipment (UE), an authentication challenge to be verified the authentication challenge in the UE,
        receive, from the UE, a first register message including an access token to authenticate the UE in the SIP core and to authenticate the UE in a mission critical push to talk (MCPTT) server, and
        transmit, to the MCPTT server, a second register message including the access token to authenticate the UE in the MCPTT server in case that a successful SIP authentication is performed based on the first register message.

10. The SIP core of claim 9, wherein an IP multimedia public user identity (IMPU) is bound with a MCPTT ID by the MCPTT server when the MCPTT server receives the second register message.

11. The SIP core of claim 9, wherein the first register message and the second register message include a parameter to authenticate the UE in the MCPTT server respectively.

12. The SIP core of claim 9, wherein an IP multimedia public user identity (IMPU) is bound with a MCPTT ID by the MCPTT server when the MCPTT server receives the second register message.

* * * * *